United States Patent
Marcelpoil et al.

(10) Patent No.: US 11,988,596 B2
(45) Date of Patent: May 21, 2024

(54) SYSTEMS AND METHODS FOR IMAGING AND IMAGE-BASED ANALYSIS OF TEST DEVICES

(71) Applicant: Becton, Dickinson and Company, Franklin Lakes, NJ (US)

(72) Inventors: Raphael Marcelpoil, Saint Pierre de Chartreuse (FR); John Page, White Hall, MD (US); Jean-Marc Volle, Coublevie (FR); Cedrick Orny, Grenoble (FR); Carmelo Tricoli, Grenoble (FR); Mathieu Fernandes, Coublevie (FR)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 394 days.

(21) Appl. No.: 17/451,743

(22) Filed: Oct. 21, 2021

(65) Prior Publication Data
US 2022/0128455 A1 Apr. 28, 2022

Related U.S. Application Data

(60) Provisional application No. 63/126,437, filed on Dec. 16, 2020, provisional application No. 63/105,146, filed on Oct. 23, 2020.

(51) Int. Cl.
*G01N 21/01* (2006.01)
*G01N 33/543* (2006.01)
*G06T 7/00* (2017.01)

(52) U.S. Cl.
CPC ....... *G01N 21/01* (2013.01); *G01N 33/54388* (2021.08); *G06T 7/0002* (2013.01);
(Continued)

(58) Field of Classification Search
CPC .............. G01N 21/01; G01N 33/54388; G06T 7/0002; G06T 2207/10024; G06T 2207/30168; G06T 2207/30204
See application file for complete search history.

(56) References Cited

U.S. PATENT DOCUMENTS

| 4,843,377 A | 6/1989 | Fuller et al. |
| 4,976,923 A | 12/1990 | Lipsky et al. |

(Continued)

FOREIGN PATENT DOCUMENTS

| CN | 206489079 U | 9/2017 |
| EP | 1963828 B1 | 9/2008 |

(Continued)

OTHER PUBLICATIONS

Blake et al., "Diagnosis of porphyria—Recommended methods for peripheral laboratories". Clin Biochem Rev. May 31, 1992;13(Suppl 1): S1-S24.

(Continued)

*Primary Examiner* — David F Dunphy
(74) *Attorney, Agent, or Firm* — Knobbe, Martens, Olson & Bear LLP

(57) ABSTRACT

Systems and methods for imaging and image-based analysis of test devices can include a background device for a lateral flow assay test strip. In one aspect, the background device can include a test strip portion sized and shaped to guide placement, on the background device, of the lateral flow assay test strip; a background portion at least partially surrounding the test strip portion; and one or more features of the background portion. The one or more features can include line detection fiducials, position fiducials, modulation transfer function fiducials, motion blur detection fiducials, and/or RGB balanced areas for evaluation of lighting conditions.

30 Claims, 11 Drawing Sheets
(4 of 11 Drawing Sheet(s) Filed in Color)

(52) U.S. Cl.
CPC .............. *G06T 2207/10024* (2013.01); *G06T 2207/30168* (2013.01); *G06T 2207/30204* (2013.01)

(56) References Cited

U.S. PATENT DOCUMENTS

| | | | |
|---|---|---|---|
| 5,119,830 A | 6/1992 | Davis | |
| 5,260,219 A | 11/1993 | Fritz | |
| 5,360,013 A | 11/1994 | Gilbert | |
| 5,408,535 A | 4/1995 | Howard, III et al. | |
| 5,470,750 A | 11/1995 | Bar-Or | |
| 5,501,837 A | 3/1996 | Sayles | |
| 5,595,187 A | 1/1997 | Davis | |
| 5,976,469 A | 11/1999 | Davis | |
| D457,246 S | 5/2002 | Mazel et al. | |
| 6,514,461 B1 | 2/2003 | Lappe et al. | |
| 6,565,814 B1 | 5/2003 | Anraku et al. | |
| 7,097,103 B2 | 8/2006 | Tseng | |
| 7,190,818 B2 | 3/2007 | Ellis et al. | |
| 7,197,169 B2 | 3/2007 | Wang | |
| 7,267,799 B1 | 9/2007 | Borich et al. | |
| 7,292,718 B2 | 11/2007 | Douglass et al. | |
| 7,313,257 B2 | 12/2007 | Roman | |
| 7,344,081 B2 | 3/2008 | Tseng | |
| 7,420,663 B2 | 9/2008 | Wang et al. | |
| 7,428,325 B2 | 9/2008 | Douglass et al. | |
| 7,474,390 B2 | 1/2009 | Robinson et al. | |
| 7,622,729 B2 | 11/2009 | Duesbury | |
| 7,652,268 B2 | 1/2010 | Patel | |
| D633,209 S | 2/2011 | Boessneck et al. | |
| D637,310 S | 5/2011 | Barbieux et al. | |
| 8,068,666 B2 | 11/2011 | Gregory et al. | |
| 8,073,248 B2 | 12/2011 | Brunner et al. | |
| 8,145,431 B2 | 3/2012 | Kloepfer et al. | |
| 8,150,115 B2 | 4/2012 | Capewell | |
| 8,268,636 B2 | 9/2012 | Nazareth et al. | |
| 8,506,901 B2 | 8/2013 | Chen et al. | |
| D690,828 S | 10/2013 | Yoon et al. | |
| 8,655,009 B2 | 2/2014 | Chen et al. | |
| 8,814,531 B2 | 6/2014 | Raasch | |
| D712,060 S | 8/2014 | Tippett et al. | |
| 8,809,066 B2 | 8/2014 | Matsumoto | |
| 8,877,140 B2 | 11/2014 | Chen et al. | |
| 8,889,424 B2 | 11/2014 | Ehrenkranz et al. | |
| 8,911,679 B2 | 12/2014 | Chen et al. | |
| 8,916,390 B2 | 12/2014 | Ozean et al. | |
| 8,976,252 B2 | 3/2015 | Koh et al. | |
| 8,998,613 B2 | 4/2015 | Jung et al. | |
| 8,999,728 B2 | 4/2015 | Nazareth et al. | |
| 9,042,630 B2 | 5/2015 | Binnig et al. | |
| 9,063,091 B2 | 6/2015 | Tsai et al. | |
| 9,230,187 B2 | 1/2016 | Hamsici et al. | |
| 9,240,039 B2 | 1/2016 | Cong et al. | |
| 9,285,323 B2 | 3/2016 | Burg et al. | |
| 9,307,214 B1 | 4/2016 | Liu et al. | |
| 9,354,181 B2 | 5/2016 | Barstis et al. | |
| 9,386,221 B2 | 7/2016 | Kauniskangas et al. | |
| 9,445,749 B2 | 9/2016 | Erickson et al. | |
| 9,466,103 B2 | 10/2016 | Athelogou et al. | |
| 9,466,104 B2 | 10/2016 | Tsai et al. | |
| 9,489,703 B2 | 11/2016 | Kauniskangas et al. | |
| 9,525,867 B2 | 12/2016 | Thomas et al. | |
| 9,532,060 B2 | 12/2016 | Mesh-Iliescu et al. | |
| 9,554,109 B2 | 1/2017 | Yao | |
| 9,569,858 B2 | 2/2017 | Babcock et al. | |
| 9,600,878 B2 | 3/2017 | Tsai et al. | |
| 9,607,380 B2 | 3/2017 | Burg et al. | |
| 9,686,540 B2 | 6/2017 | Zhou et al. | |
| 9,689,803 B1 | 6/2017 | Ruttner | |
| 9,756,324 B1 | 9/2017 | Flanagan et al. | |
| 9,778,200 B2 | 10/2017 | Tsai et al. | |
| 9,787,815 B2 | 10/2017 | Erickson et al. | |
| 9,818,193 B2 | 11/2017 | Smart | |
| 9,824,441 B2 | 11/2017 | Satish et al. | |
| 9,833,783 B1 | 12/2017 | Klein et al. | |
| 9,857,372 B1 | 1/2018 | Pulitzer et al. | |
| 9,857,373 B1 | 1/2018 | Pulitzer et al. | |
| 9,863,811 B2 | 1/2018 | Burg et al. | |
| 9,888,186 B2 | 2/2018 | Zhou et al. | |
| 9,903,857 B2 | 2/2018 | Polwart et al. | |
| 9,933,359 B2 | 4/2018 | Zehler et al. | |
| 9,978,153 B2 | 5/2018 | Kisner et al. | |
| 9,990,560 B2 | 6/2018 | Decker et al. | |
| 10,019,656 B2 | 7/2018 | Huang et al. | |
| 10,055,837 B2 | 8/2018 | Lee et al. | |
| 10,068,329 B2 | 9/2018 | Adiri et al. | |
| 10,088,411 B2 | 10/2018 | Shyam et al. | |
| 10,089,753 B1 | 10/2018 | Fegyver et al. | |
| 10,101,342 B2 | 10/2018 | Nazareth et al. | |
| 10,132,802 B2 | 11/2018 | Ehrenkranz | |
| 10,168,322 B2 | 1/2019 | Nazareth et al. | |
| 10,175,162 B2 | 1/2019 | Jia et al. | |
| 10,210,626 B2 | 2/2019 | Chiba et al. | |
| 10,267,743 B2 | 4/2019 | Burg et al. | |
| 10,331,924 B2 | 6/2019 | Pulitzer et al. | |
| 10,352,946 B2 | 7/2019 | Nazareth et al. | |
| 10,354,166 B2 | 7/2019 | Nahum et al. | |
| 10,354,412 B2 | 7/2019 | Kisner et al. | |
| D857,228 S | 8/2019 | Kaplan et al. | |
| 10,395,368 B2 | 8/2019 | Berezhna et al. | |
| 10,473,659 B2 | 11/2019 | Pulitzer et al. | |
| 10,477,175 B2 | 11/2019 | Ogasawara et al. | |
| 10,498,936 B2 | 12/2019 | Ehrenkranz | |
| 10,527,555 B2 | 1/2020 | Pulitzer et al. | |
| 10,559,081 B2 | 2/2020 | Omer et al. | |
| 10,571,395 B2 | 2/2020 | Karlovac et al. | |
| D879,999 S | 3/2020 | Wronko | |
| 10,605,741 B2 | 3/2020 | Lu et al. | |
| 10,635,870 B2 | 4/2020 | Pulitzer et al. | |
| 10,636,527 B2 | 4/2020 | Pulitzer et al. | |
| 10,663,466 B2 | 5/2020 | Ozean et al. | |
| D886,901 S | 6/2020 | Hussey et al. | |
| 10,670,533 B2 | 6/2020 | Nazareth et al. | |
| 10,681,516 B2 | 6/2020 | Zin et al. | |
| 10,753,932 B2 | 8/2020 | Hopper | |
| 10,769,489 B2 | 9/2020 | Nahum et al. | |
| 10,796,183 B2 | 10/2020 | Topal et al. | |
| 10,835,122 B2 | 11/2020 | Pulitzer et al. | |
| 10,890,534 B2 | 1/2021 | Pulitzer et al. | |
| 10,943,368 B1 * | 3/2021 | Ha | H04N 17/002 |
| 10,948,352 B2 | 3/2021 | Burg | |
| D915,618 S | 4/2021 | Heron | |
| 10,983,065 B2 | 4/2021 | Burg | |
| 10,991,096 B2 | 4/2021 | Adiri et al. | |
| 11,026,624 B2 | 6/2021 | Adiri et al. | |
| 11,030,778 B2 | 6/2021 | Burg et al. | |
| 11,087,467 B2 | 8/2021 | Adiri et al. | |
| 11,107,585 B2 | 8/2021 | Pulitzer et al. | |
| 11,112,406 B2 | 9/2021 | Pulitzer et al. | |
| 11,120,235 B2 | 9/2021 | Pulitzer et al. | |
| D970,033 S | 11/2022 | Marcelpoil et al. | |
| 2003/0108450 A1 | 6/2003 | Mainquist et al. | |
| 2005/0221504 A1 | 10/2005 | Petruno et al. | |
| 2007/0026530 A1 | 2/2007 | Wu et al. | |
| 2007/0196862 A1 | 8/2007 | Wang | |
| 2008/0287316 A1 | 11/2008 | Spivey et al. | |
| 2015/0211987 A1 | 7/2015 | Burg et al. | |
| 2015/0254844 A1 | 9/2015 | Tsai et al. | |
| 2015/0325006 A1 | 11/2015 | Adiri et al. | |
| 2016/0139156 A1 | 5/2016 | Lakdawala et al. | |
| 2016/0222373 A1 | 8/2016 | Jia | |
| 2016/0245793 A1 | 8/2016 | Samsoondar | |
| 2016/0281150 A1 | 9/2016 | Rawlings et al. | |
| 2016/0300420 A1 | 10/2016 | Li et al. | |
| 2018/0190373 A1 | 7/2018 | Pulitzer et al. | |
| 2018/0196037 A1 | 7/2018 | Polwart et al. | |
| 2018/0259449 A1 | 9/2018 | Poulsen et al. | |
| 2018/0364224 A1 | 12/2018 | Pulitzer et al. | |
| 2018/0372717 A1 | 12/2018 | Tu et al. | |
| 2019/0148014 A1 | 5/2019 | Pulitzer et al. | |
| 2019/0302009 A1 | 10/2019 | Borich et al. | |
| 2019/0376966 A1 | 12/2019 | Pulitzer et al. | |
| 2020/0126227 A1 | 4/2020 | Adiri et al. | |
| 2020/0242769 A1 | 7/2020 | Limburg | |

(56) References Cited

U.S. PATENT DOCUMENTS

| | | |
|---|---|---|
| 2020/0286600 A1 | 9/2020 | De Brouwer et al. |
| 2020/0319140 A1 | 10/2020 | Saratkar et al. |
| 2021/0016280 A1 | 1/2021 | Flesher |
| 2021/0089814 A1 | 3/2021 | Lopes et al. |
| 2021/0142890 A1 | 5/2021 | Adiri et al. |
| 2021/0231574 A1 | 7/2021 | Wang et al. |
| 2022/0084659 A1 | 3/2022 | Rowe et al. |
| 2023/0095831 A1* | 3/2023 | Ehrenkranz .......... G01N 33/558 435/287.2 |

FOREIGN PATENT DOCUMENTS

| | | | |
|---|---|---|---|
| EP | 3477270 | A1 | 5/2019 |
| EP | 3581921 | A1 | 12/2019 |
| EP | 3591385 | A1 | 1/2020 |
| EP | 3651162 | A1 | 5/2020 |
| KR | 101492972 | B1 | 2/2015 |
| WO | WO 2012/131386 | A1 | 10/2012 |
| WO | WO 2013/116831 | A1 | 8/2013 |
| WO | WO 2014/025415 | A2 | 2/2014 |
| WO | WO 2014/057159 | A1 | 4/2014 |
| WO | WO 2014/178062 | A2 | 11/2014 |
| WO | WO 2017/138946 | A1 | 8/2017 |
| WO | WO 2017/140686 | A1 | 8/2017 |
| WO | WO 2019/153934 | A1 | 8/2019 |
| WO | WO 2019/162496 | A1 | 8/2019 |
| WO | WO 2019/215199 | A1 | 11/2019 |
| WO | WO 2019/238500 | A1 | 12/2019 |
| WO | WO 2019/246361 | A1 | 12/2019 |
| WO | WO 2020/016616 | A1 | 1/2020 |
| WO | WO 2020/089188 | A1 | 5/2020 |
| WO | WO 2020/161238 | A1 | 8/2020 |
| WO | WO 2020/165456 | A1 | 8/2020 |
| WO | WO 2021/55127 | A1 | 8/2021 |
| WO | WO 2021/155082 | A1 | 8/2021 |
| WO | WO 2021/155103 | A1 | 8/2021 |
| WO | WO 2021/155105 | A1 | 8/2021 |
| WO | WO 2021/155153 | A1 | 8/2021 |
| WO | WO 2021/155170 | A1 | 8/2021 |

OTHER PUBLICATIONS

Comstock J., "Healthy.io gets FDA nod for smartphone camera-based home urine test". Jul. 25, 2018; Retrieved from internet on Nov. 18, 2021 at: https://www.mobihealthnews.com/content/healthyio-gets-fda-nod-smartphone-camera-based-home-urine-test in 2 pages.

Deacon et al., "Identification of acute porphyria: Evaluation of a commercial screening test for urinary porphobilinogen". Ann Clin Biochem., Nov. 1, 1998;35(6): 726-732.

Gorchein A., "Testing for porphobilinogen in urine," Clin Chem. Mar. 1, 2002;48(3): 564-566.

healthy.io; (2020) Turning the smartphone into a medical device, downloaded from the Internet on Jan. 8, 2021, URL: https://healthy.io/services/maternity/ in 3 pages.

Mauzerall et al., "The occurrence and determination of σ-aminolevulinic acid and porphobilinogen in urine," J Biol Chem. Mar. 1956;219(156): 435-446.

Min et al., "Development of a smartphone-based lateral-flow imaging system using machine-learning classifiers for detection of *Salmonella* spp". J Microbiol Meth. Sep. 1, 2021;188: 106288 in 8 pages.

Moore et al., "A quantitative assay for urinary porphobilinogen," Clin Chem. Dec. 1, 1964;10(12): 1105-1111.

Roshal et al., "Rapid quantitative method using spin columns to measure porphobilinogen in urine," Clin Chem. Feb. 1, 2008;54(2): 429-431.

Scanwell Health, "At-Home UTI Test—Know if you have a UTI in 2 minutes", downloaded Jan. 8, 2021 from https://www.scanwellhealth.com/uti in 9 pages.

Thermo Fisher, "Porphobilinogen (PBG) Test Kit", Insert for Catalogue No. TR52001, Dec. 31, 2011; 2 pages.

Vogeser et al., "Evaluation of a commercially available rapid urinary porphobilinogen test," Clin Chem Lab Med. Jan. 1, 2011;49(9): 1491-1494.

International Search Report and Written Opinion dated Dec. 30, 2011 for Application No. PCT/US2011/001581 in 9 pages.

International Search Report and Written Opinion dated May 21, 2012 for Application No. PCT/US2011/059227 in 8 pages.

International Search Report and Written Opinion dated Mar. 24, 2021 for Application No. PCT/US2020/060579 in 16 pages.

International Search Report and Written Opinion dated Jan. 24, 2022 for Application No. PCT/US2021/055963 in 14 pages.

International Search Report and Written Opinion dated Jun. 22, 2021 for Application No. PCT/US2021/025789 in 11 pages.

Becton, Dickinson and Company, "BD Receives Emergency Use Authorization for First At-Home COVID-19 Test to Use Smartphone to Interpret, Deliver Results", BD Press Release; Aug. 25, 2021; available online at https://news.bd.com/2021-08-25-BD-Receives-Emergency-Use-Authorization-for-First-At-Home-COVID-19-Test-to-Use-Smartphone-to-Interpret,-Deliver-Results; 2 pages.

* cited by examiner

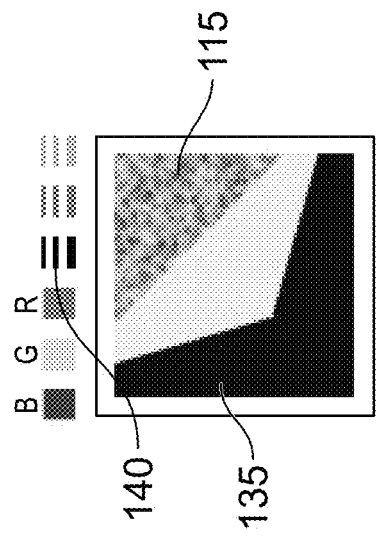
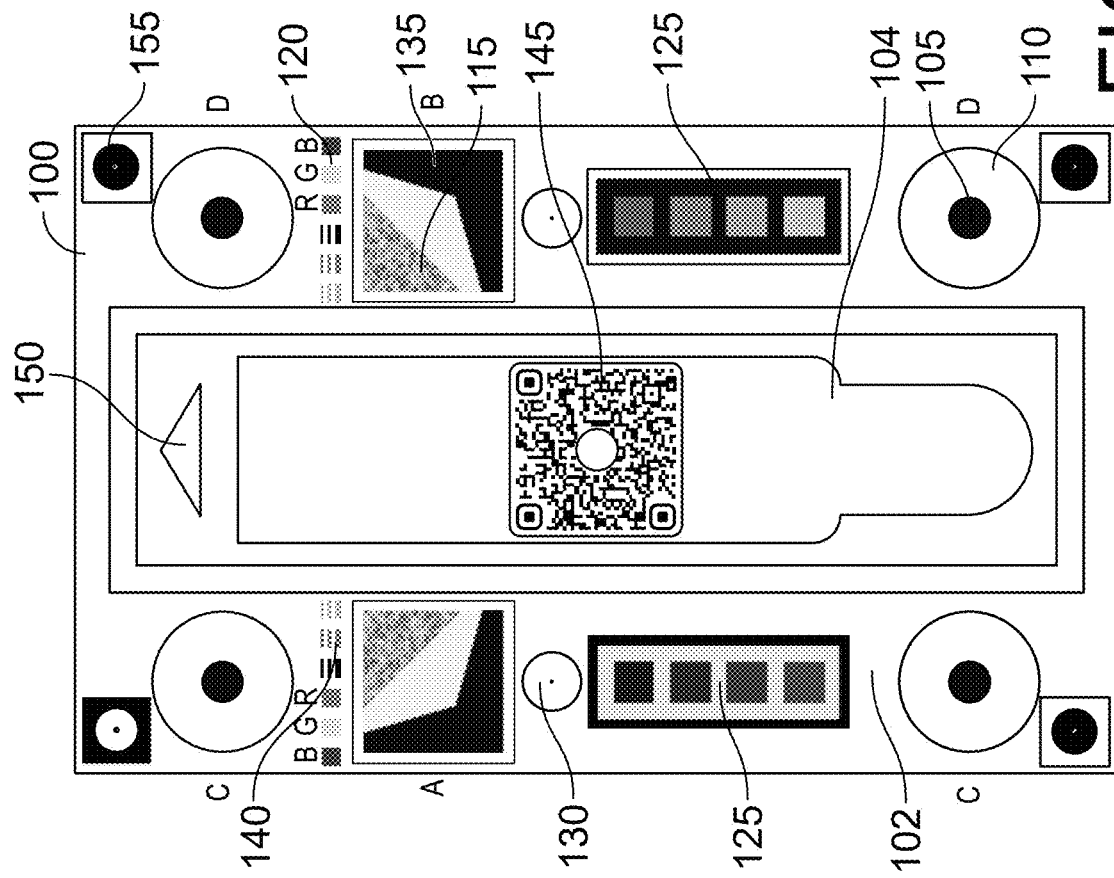
FIG. 1B
FIG. 1C
FIG. 1D
FIG. 1A

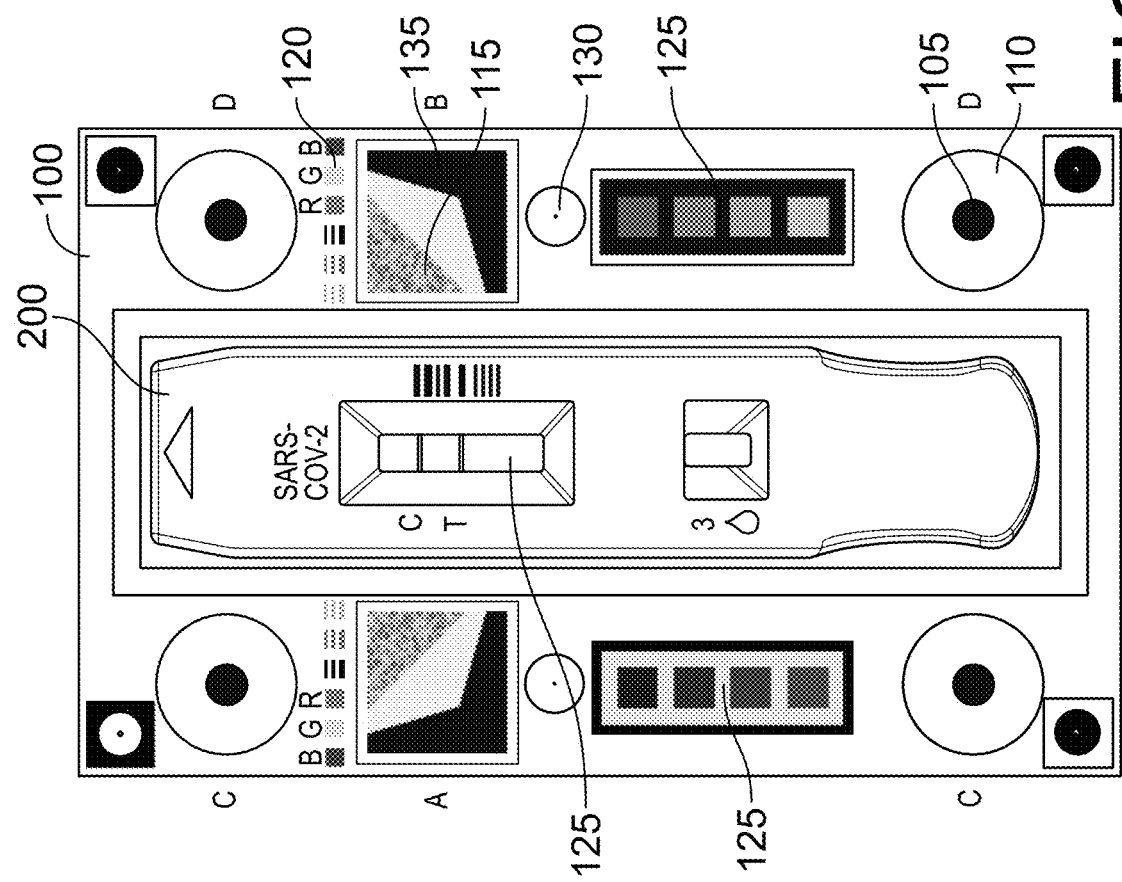
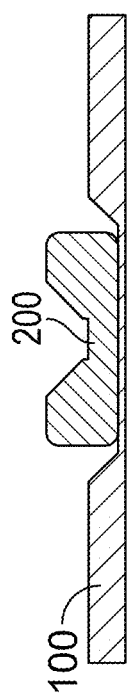
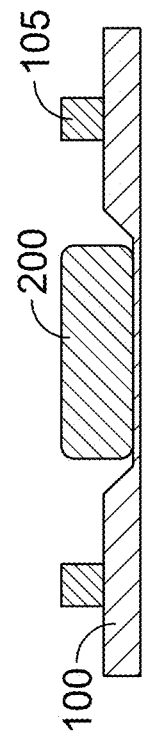
FIG. 2B
FIG. 2C
FIG. 2A

SYSTEMS AND METHODS FOR IMAGING AND IMAGE-BASED ANALYSIS OF TEST DEVICES

CROSS-REFERENCE TO RELATED APPLICATIONS

This application claims the benefit of U.S. Provisional Application Ser. No. 63/105,146, filed Oct. 23, 2020, titled SYSTEMS AND METHODS FOR IMAGING AND IMAGE-BASED ANALYSIS OF DIAGNOSTIC TEST DEVICES, and U.S. Provisional Application Ser. No. 63/126,437, filed Dec. 16, 2020, titled SYSTEMS AND METHODS FOR IMAGING AND IMAGE-BASED ANALYSIS OF TEST DEVICES, both of which are incorporated by reference herein in their entirety.

TECHNICAL FIELD

The present technology relates to analyte testing, and more particularly to applications and test cartridge background devices for reading of cartridge analysis information.

BACKGROUND

Test analysis information may be obtained from images of testing devices such as lateral flow assays or other cartridge-based tests. Determination of analysis information based on image analysis may be susceptible to error based on color management, alignment, image warping, and other sources of error within the captured images. For example, such methods may be susceptible to reading errors such as false negative results due to degraded image quality (e.g., high noise level, bad illumination, poor focus, significant motion blur, etc.) and/or algorithmic errors (e.g., bad homography, bad normalization, etc.). Analysis of images captured by a camera of a smartphone or other mobile device may be especially susceptible to such errors.

SUMMARY

To limit the occurrence of errors in image-based test analysis systems, imaging systems for test analysis are usually operated in very controlled environments and carefully calibrated and normalized. When a calibrated and controlled environment is not available, image qualification and normalization metrics may need to be extracted from the image itself. Accordingly, the present technology provides systems and methods for including additional contextual information with known characteristics (e.g., size, intensity, color, spatial frequencies, contrast, and the like) in the captured scene, together with the test device itself. Systems and methods of the present technology include, among other aspects, 3-dimensional cartridge background device (e.g., trays or cards) on which a test cartridge can be positioned prior to taking an image of the cartridge for information analysis, to serve as a background for the image. The present technology further includes applications, such as mobile device applications, configured to perform image analysis on images of a cartridge after standardization and normalization of the image using the 3D background device. The background may contain one or more fiducials to facilitate the evaluation of image acquisition metrics based on the image. In some embodiments, some or all fiducials may be located in the same plane as a surface of a test strip, such as a test surface of a lateral flow assay test strip, and/or in the same plane as a surface of a cartridge containing the test strip, to allow a refined image capture, leading to image acquisition conditions validation, image normalization, and/or image standardization prior to analysis using evaluation software or manual interpretation. The 3D design of the 3D background devices disclosed herein can further allow for de-warping of images taken at an angle other than a top plan view of the cartridge and 3D background device.

In one non-limiting example, a background device for an assay test strip is provided. The background device includes a test strip portion sized and shaped to guide placement, on the background device, of a lateral flow assay test strip; a background portion at least partially surrounding the test strip portion; and a plurality of line detection fiducials disposed on the background portion, each of the plurality of line detection fiducials having a color that is different than a color of a surrounding area of the background portion and a width associated with an expected width of a line on the lateral flow assay test strip.

The plurality of line detection fiducials can include at least a first line detection fiducial having a width substantially equal to the expected width and a second line detection fiducial having a width greater than or less than the expected width. The plurality of line detection fiducials can include at least a first line detection fiducial and a second line detection fiducial having a first shade of a color. The plurality of line detection fiducials can include at least a third line detection fiducial having a second shade of the color that is lighter or darker than the first shade of the color. In one example, the color is grey and an expected color of the line on the lateral flow assay test strip is not grey.

The background device can also include one or more motion blur detection fiducials, each of the one or more motion blur detection fiducials including a dot of a first color surrounded by a region of a second color contrasting with the first color. The background device can also include at least three position fiducials disposed on the background portion proximate to corners of the background portion to facilitate detection of at least one of a position, tilt, or roll of an image capture device relative to the background device. In one example, the background portion includes a red-green-blue (RGB) balanced area having a color corresponding to equal red, green, and blue values in an RGB color space.

The test strip portion can include alignment indicia configured to facilitate placement of the lateral flow assay test strip on the test strip portion of the background device. The test strip portion can include a computer-readable code positioned to be covered when the lateral flow assay test strip is placed on the test strip portion, the computer-readable code identifying a software application configured to analyze, based at least in part on the line detection fiducials, whether an image of the lateral flow assay test strip qualifies for further analysis. The test strip portion can include a computer-readable code positioned to be covered when the lateral flow assay test strip is placed on the test strip portion, the computer-readable code identifying a software application configured to analyze an image of the lateral flow assay test strip to determine a test result based at least in part on the line detection fiducials. The background device can be a 3-dimensional background device including one or more recesses or one or more 3-dimensional features protruding from the background portion. The lateral flow assay test strip can be housed in a cartridge, and the test strip portion can be sized and shaped to guide placement of the cartridge on the test strip portion of the background device. Each of the plurality of line detection fiducials can have a width associated with an expected width of at least one of: a test line that changes intensity or color in the presence of an analyte of interest in a sample applied to the lateral flow assay test strip; and a control line that changes intensity or color in the presence of the sample applied to the lateral flow assay test strip.

In another non-limiting example, a computer-implemented method of determining a test result is provided. The method can include capturing, by an image capture device, an image of a lateral flow assay test strip disposed on a test strip portion of a background device, the background device including a background portion at least partially surrounding the test strip portion. The method can also include detecting, by one or more processors based at least in part on the image, a plurality of line detection fiducials disposed on the background portion of the background device, each of the plurality of line detection fiducials having a color that is different than a color of a surrounding area of the background portion and a width associated with an expected width of a line on the lateral flow assay strip. The method can further include detecting, by the one or more processors based at least in part on the image, one or more control lines or test lines on the lateral flow assay test strip based at least in part on the plurality of line detection fiducials. The method can also include determining, by the one or more processors, a test result of the lateral flow assay test strip based at least in part on the one or more detected control lines or test lines.

The method can also include, prior to capturing the image, analyzing that an image taken by the image capture device qualifies or does not qualify for detection of the test result. Detecting one or more control lines or test lines can include detecting a presence of the one or more control lines or test lines based at least in part on a width of at least one of the plurality of line detection fiducials. The plurality of line detection fiducials can include at least a first line detection fiducial and a second line detection fiducial having a first shade of a color and a third line detection fiducial having a second shade of the color that is lighter or darker than the first shade of the color, and detecting one or more control lines or test lines can include detecting an intensity or a color of the one or more control lines or test lines based at least in part on the first, second, or the third line detection fiducial. In one example, the color of the first, second, and third fiducial is grey and the color of the one or more control lines or test lines is not grey.

The background portion of the background device can include a red-green-blue (RGB) balanced area having a color corresponding to equal red, green, and blue values in an RGB color space. The method can also include, prior to determining the test result, evaluating an illumination condition of the background device based at least in part on the RGB balanced area. Evaluating the illumination condition can include also at least one of a glare or a shadow on the RGB balanced area. The method can also include, prior to determining the test result, evaluating a modulation transfer function of the image capture device based at least in part on the plurality of line detection fiducials or on one or more additional fiducials on the background portion of the background device. The method can also include estimating a level of detection based on the modulation transfer function, wherein the test result of the lateral flow assay is determined based at least in part on the estimated level of detection. The method can also include, prior to determining the test result, detecting a level of motion blur of the image based at least in part on one or more motion blur detection fiducials disposed on the background portion of the background device. Each of the one or more motion blur detection fiducials can include a dot of a first color surrounded by a region of a second color contrasting with the first color. The method can also include, prior to determining the test result, determining at least one of a position, a tilt, or a roll of the image capture device relative to the background device based at least in part on a plurality of position fiducials disposed on the background portion of the background device.

BRIEF DESCRIPTION OF THE DRAWINGS

The patent or application file contains at least one drawing executed in color. Copies of this patent or patent application with color drawing(s) will be provided by the Office upon request and payment of the necessary fee.

FIG. 1A is a top plan view illustrating an example 3D cartridge background device in accordance with the present technology.

FIGS. 1B and 1C are cross-sectional views of the example 3D cartridge background device of FIG. 1A.

FIG. 1D is an enlarged view of a portion of the example background device of FIGS. 1A-1C illustrating example fiducials thereon.

FIG. 2A is a top plan view illustrating the placement of a test cartridge against the example 3D cartridge background device of FIGS. 1A-1C.

FIGS. 2B and 2C are cross-sectional views of the test cartridge and example 3D cartridge background device of FIG. 2A.

DETAILED DESCRIPTION

Figure 3:
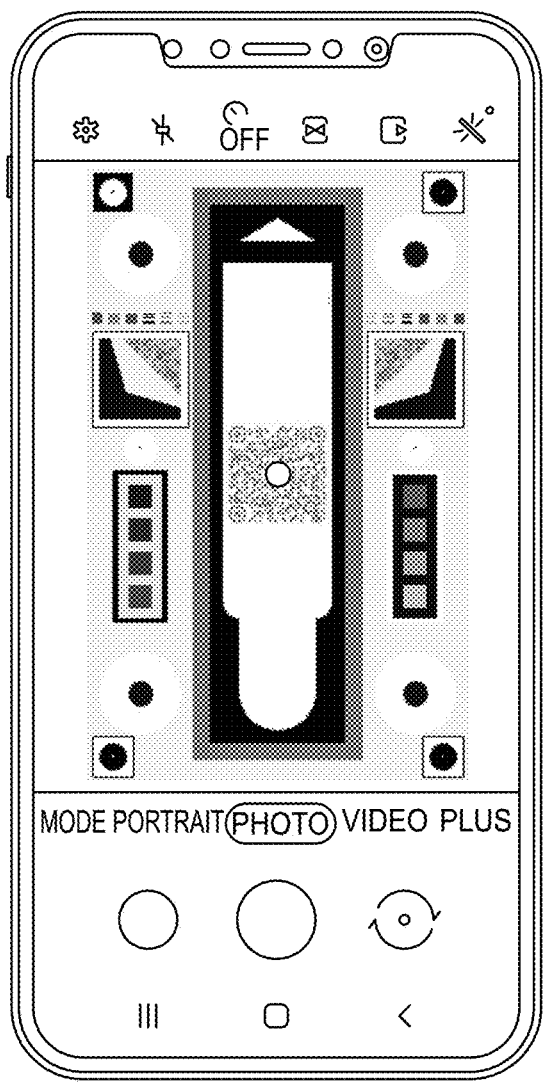
FIGS. 3 and 4 illustrate a graphical user interface (GUI) of a mobile device application displaying images of the example 3D cartridge background devices of FIGS. 1A and 2A, respectively.

Embodiments of the present disclosure relate to systems and techniques for detection of analytes of interest that may be present in biological or non-biological samples such as fluids. Analytes of interest may include any detectable substances such as but not limited to antibodies, proteins, haptens, nucleic acids, amplicons, hormones, and hazardous or non-hazardous drugs or contaminants such as antineoplastic drugs used in the treatment of cancer. Throughout this disclosure, example systems, devices, and methods will be described with reference to collection, testing, and detection of analytes such as those relevant for diagnostic testing related to infectious diseases, but it will be understood that the present technology can be used to collect, test, and detect any particle, molecule, or analyte of interest. Test strips and/or cartridges as described herein may be configured for performance of diagnostic and/or non-diagnostic tests. In some embodiments, embodiments of the present disclosure can be implemented in conjunction with systems such as the BD Veritor System for Rapid Detection of SARS CoV-2, the BD Veritor System for Rapid Detection of Flu A+B, the BD Veritor System for Rapid Detection of Respiratory Syncytial Virus (RSV), the BD Veritor System for Rapid Detection of Group A Strep, the BD Veritor system, the BD Veritor Plus system, and/or components or operations thereof.

Systems and methods of the present technology include, among other aspects, 3-dimensional cartridge background device (e.g., trays or cards) on which a test cartridge can be positioned prior to taking an image of the cartridge for cartridge information analysis, to serve as a background for the image. The present technology further includes applications, such as mobile device applications, configured to perform image analysis on images of a cartridge and 3D background device. The background may contain one or more fiducials to facilitate the evaluation of image acquisition metrics based on the image. In some embodiments, some or all fiducials may be located in the same plane as a test surface of a test strip, such as a test surface of a lateral flow assay test strip, to allow a refined image capture, leading to image acquisition conditions validation, image normalization, and/or image standardization prior to analysis using evaluation software or manual interpretation. The 3D design of the 3D background devices disclosed herein can further allow for de-warping of images taken at an angle other than a top plan view of the cartridge and 3D background device.

Prior to analyzing an assay and establishing a result for an analyzed image, some pre-processing steps may be desirable. In some aspects, assessment of image metrics can first be performed such as to determine the suitability of an image and/or to select a best image from a plurality of images taken of the test device. Correction and qualification steps may come next. In some embodiments, a series of images may be captured, and a test result may be determined from the best or most suitable image of the series. A possible embodiment describe here is to capture N images (e.g. N=3), evaluate one or a series of key metrics for each image (e.g., motion blur, shadow effects, warping, etc.) and only retain the best or optimal one (e.g., with less motion blur or other optimal characteristic(s)). This strategy can be applied to one metric or a series of metrics or all metrics considered together. Based on the preferred metrics, the best image is then considered either qualified (e.g., suitable for subsequent analysis) or disqualified (e.g., requiring the user to take another step such as to try to capture the image again). If qualified, the image can then be corrected and/or normalized such as to reduce or minimize variability due to external conditions (including, e.g., the user of the phone, illumination) as well as phone characteristics (e.g., optics, electronics, and software).

FIGS. 1A-2C illustrate an example 3D background device 100 in accordance with the present technology. FIG. 1A illustrates the 3D background device 100 alone, while FIG. 2A illustrates the 3D background device 100 with a test cartridge 200 placed thereon for imaging. FIGS. 1B and 2B are cross-sectional views taken along a line from A to B in FIGS. 1A and 2A, respectively. FIGS. 1C and 2C are cross-sectional views taken along a line from either pair of C to D in FIGS. 1A and 2A, respectively.

The 3D background device 100 generally includes a background portion 102 including one or more fiducials and a cartridge portion 104 where a cartridge 200 may be received for analysis. In some embodiments, the cartridge portion 104 may be a recess or inset to assist in proper placement of the cartridge 200.

Various example fiducials are illustrated in FIGS. 1A-2C and described herein along with their function as enablers for image metric calculations and/or for image normalization and standardization. As will be described in greater detail with reference to FIGS. 10-11B, information associated with the fiducials may be stored digitally in a background device model which can facilitate image analysis using the fiducials. For example, a background device model may store the locations of some or each of the fiducials (e.g., as one or more x, y coordinates) relative to optically detectable features of the 3D background device 100 (e.g., relative to one or more corners or alignment fiducials of the background device 100 such as additional corner fiducials 155). Thus, various embodiments of the 3D background device 100 may include more or fewer fiducials than those illustrated in FIGS. 1A-2C, in the same or different locations, with the location of each fiducial reliably determinable by an image analysis application based on a corresponding background device model.

In some embodiments, fiducials such as 4 cylinders 105, having heights matching the height of the top surface of the cartridge 200 placed within the cartridge portion 104 of the 3D background device 100, allow image processing software to evaluate the tilt and roll of the cartridge 200 within the photo so that any such tilt and roll may be corrected. Moreover, the intensity and/or direction of any shadows created by the cylinders 105 may be observed to estimate shadow impact on the test strip 205 within the cartridge 200.

In order for the exposure (e.g., exposure time) of the camera to be well adapted and avoid saturation at the strip level, parts of the scan card design may include some pure white regions 110. In order for the 3D background device 100 to facilitate standardization and/or normalization of an acquired image, one or more of the following metrics may be used individually or in combination with each other.

Focusing of the camera: In order for a suitable focus to be made on the test strip 205, a granular texture 115 may be placed on the 3D background device 100 on opposing sides of the cartridge portion 104 in the same plane as the bands to be detected on the test strip 205. This texture 115, together with some or all other fiducials in that plane, can force the focus (e.g., of an auto-focused camera such as a mobile device camera) to be mainly made in the plane of the test strip 205, not on the upper plane of the cartridge 200, therefore improving capabilities to detect even faint test lines. In some embodiments, an aid such as a "focus here" prompt overlaid on a mobile device via augmented reality may prompt a user to manually focus the mobile device camera on the granular texture 115.

Dynamic range: The design may contain regions spanning the entire dynamic range in each of the red, green, and blue color channels that may be utilized in many digital cameras. For example, in some embodiments more than 2.5% of the design may correspond to the 0 intensity (e.g., black level) and more than 2.5% may correspond to the 255 (e.g., maximum) intensity. The histogram can therefore be linearly extended on 0,255 from 2.5 percentile and 97.5 percentile in each channel.

White balance of the camera: Except for the cartridge 200 itself, the vertical cylinders 105 and small R,G,B squares 120 for color fidelity testing, the entire design may be equally R,G,B balanced. For example, R,G,B values per pixel in the remaining portion of the surface of the 3D background device can be equal, which simplifies the evaluation and correction of the white balance of the scene, regardless of the spectral characteristics of the incoming light.

Color fidelity testing: Red, green, and blue squares 120 may be provided to determine the accuracy of response in red, green, and blue color channels. The known locations of the individual colors of red, green, and blue squares 120 may further be utilized to confirm the Bayer pattern of the particular image sensor used to capture an image of the 3D background device 100 and cartridge 200.

Linearity assessment/correction, per channel: A linear response of the camera in all channels may be desirable in order to normalize and standardize images captured from different devices (e.g., optics, electronics, and/or software of smart phones, tables, and the like). In order to evaluate and correct for linearity in each of the R,G,B channels, neutral patches 125 with known expected intensity distribution may be place on the design. The intensities of the various sub-sections of the neutral patches 125 may be selected to span through the entire dynamic range (e.g., 0, 16, 32, 48, 64, 80, 96, 128, 160, 192, 224, 240, 255, or other suitable set of intensities between 0 and 255) allowing a per channel linearity lookup table to be calculated and applied for linearity correction.

Motion blur assessment, deconvolution: The 3D background device may include two white discs 130 with a circular black dot in their center specifically designed to help assess motion blur. The longer the exposure time (depending on illumination intensity), the more the image can be prone to motion blur. Recent mobile devices frequently contain image stabilization mechanisms (hardware and/or software) that seek to limit such motion blur occurrence, nevertheless the distance from lens to scene being fairly small (in the range of one to several inches), and with some mobile devices potentially lacking such mechanism, it may be important to evaluate and eventually correct for such factors. If the shape and intensity of the small black dot is spread heterogeneously across the white disc 130, it can be determined that some motion occurred during acquisition leading to motion blur. The wider the spreading, the more the motion that has occurred. If the spread is limited and the image is qualified for further analysis, deconvolution can be applied (the scene being still) to estimate the source image motion blur free.

Signal to noise ratio (SNR): The patches 125 used for linearity assessment have a known size and geometry, further allowing software to compute, once linearized, the standard deviation across all pixels expected to be of a given same intensity per design. Evaluating this standard deviation, and therefore the corresponding SNR across all the different patches, may allow the estimation of the SNR power function as a function of the normalized and linearized intensity. This SNR may be used to correctly establish the limit of detection (LOD) of a test line according to noise level.

Modulation transfer function (MTF): Focus of the image within the plane of the test strip 205 may further be assessed via horizontal and vertical MTF assessment on both sides of the bands to be detected. Together with the signal to noise ratio, the modulation transfer function may be needed to estimate the degradation of contrast to be expected due to the focus and optics quality for objects of a given size. For example, if the MTF is only 25% at the spatial frequency corresponding to the expected width of the test band, only 25% of the original signal will be present in the captured image. MTF may therefore be used in conjunction with SNR to estimate the band LOD considering the captured image. Two regions 135 allowing both an X and Y MTF estimation using vertical and horizontal slanted edges can be symmetrically placed on both sides of the control and test bands for a balanced interpolation at the strip level. These slanted edges being on both sides and in the same plane as the test strip 205, the interpolated MTF from right and left assessments is de facto the best possible estimate in the strip plane.

Band detection capability verification: Despite best efforts to qualify, normalize, and standardize images to achieve a robust precise and accurate band detection, an additional check may be desirable in some or all implementations. Small test line fiducials 140 corresponding to the expected control line and test line widths (e.g., ½ width, expected width, 2× expected width) of different intensities can be added to the design to confirm corrections efficacy. After corrections, the SNR and/or contrast measured for these lines may be used as a final qualifier to confirm the LOD to be expected from an image.

In some embodiments, a QR code 145 or other computer-readable code may be included on the 3D background device 100 to direct a user to download software, to unlock features of existing software, or to provide other functions or features related to imaging and/or interpretation of the test strip 205, and/or reporting of results of the test strip 205. In one example, the QR code 145 is used to load the proper version of the application and/or background device model for the 3D background device 100. A barcode or other computer-readable code may be present on the cartridge 200, and may be used to select and/or confirm an algorithm used for proper assessment of the particular test to be analyzed.

An arrow 150 may further be included in the cartridge area to assist a user with proper cartridge placement and/or orientation.

Additional corner fiducials 155 arranged in a rectangular configuration can be detectable to verify the analysis window within an image and to help with tilt and roll assessment.

Figure 4:
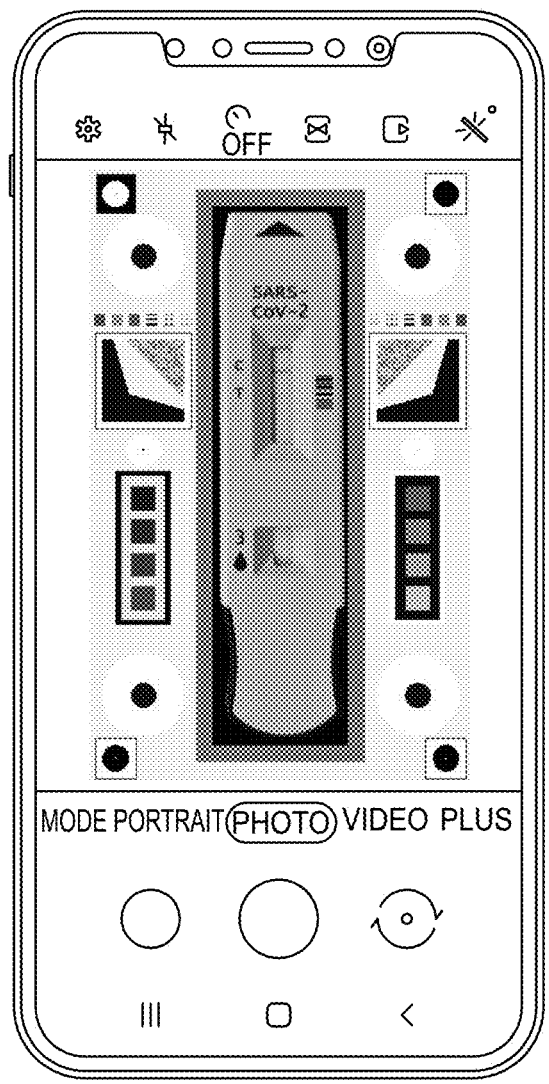

FIGS. 3 and 4 illustrate a graphical user interface (GUI) of a mobile device application displaying images of the example 3D cartridge background devices of FIGS. 1A and 2A, respectively. The GUI may be implemented in an application executing on any suitable mobile device. The application may further include augmented reality features to guide image acquisition and/or interaction with the user. For example, as shown in FIGS. 3 and 4, the application may include photo capture capability. The application may further be configured for the image analysis described herein and/or for sharing of data with health institutions (e.g., GPS, test results, etc.) for real time pandemic assessment.

Figure 5:
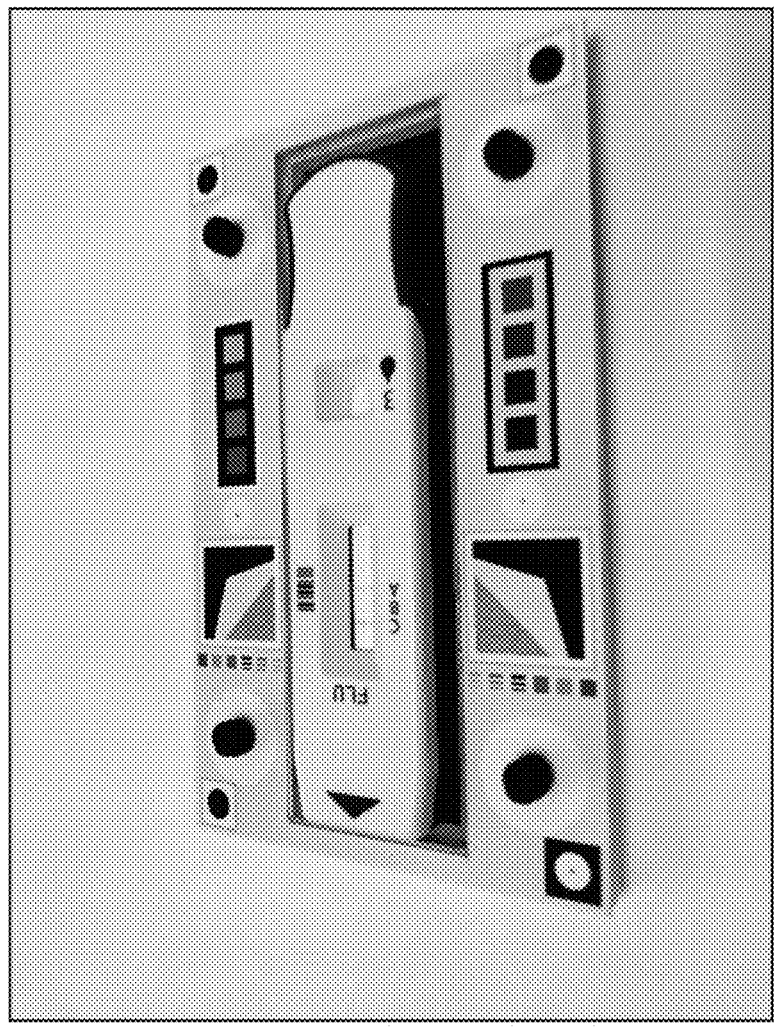
FIG. 5 is an example image of a test cartridge on a 3D cartridge background device as taken at an angle by a mobile device camera.

FIG. 5 is an example image of a test cartridge on a 3D cartridge background device as taken at an angle by a mobile device camera.

Figure 6:
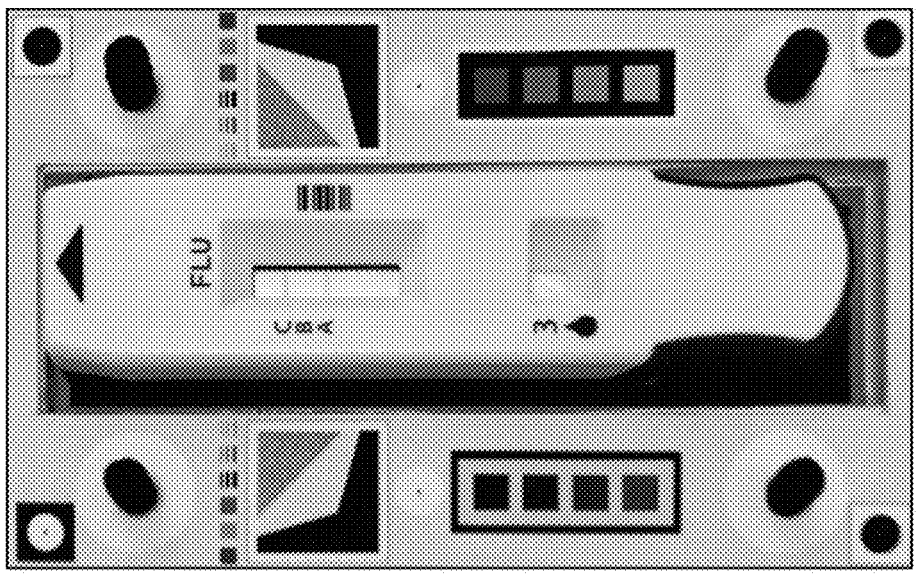
FIG. 6 is a de-warped version of the image of FIG. 5 generated by the image analysis software disclosed herein based on the fiducials of the 3D cartridge background device.

FIG. 6 is a de-warped version of the image of FIG. 5 generated by the image analysis software disclose herein based on the fiducials of the 3D cartridge background device.

Figure 7:
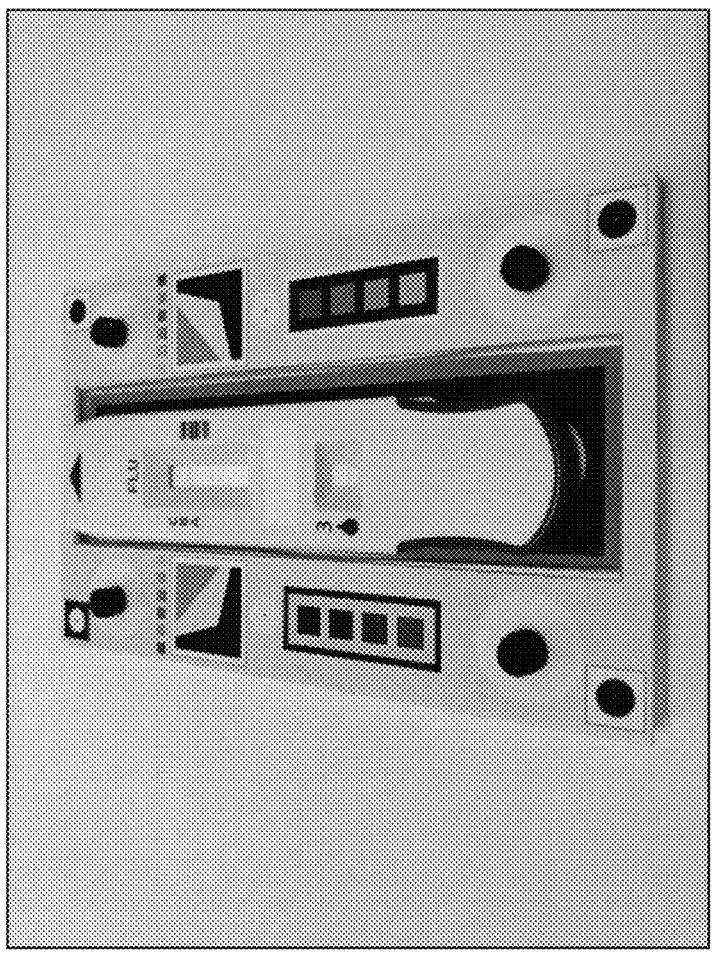
FIG. 7 is an example image of a test cartridge on a 3D cartridge background device as taken at an angle by a mobile device camera.

FIG. 7 is an example image of a test cartridge on a 3D cartridge background device as taken at an angle by a mobile device camera.

Figure 8:
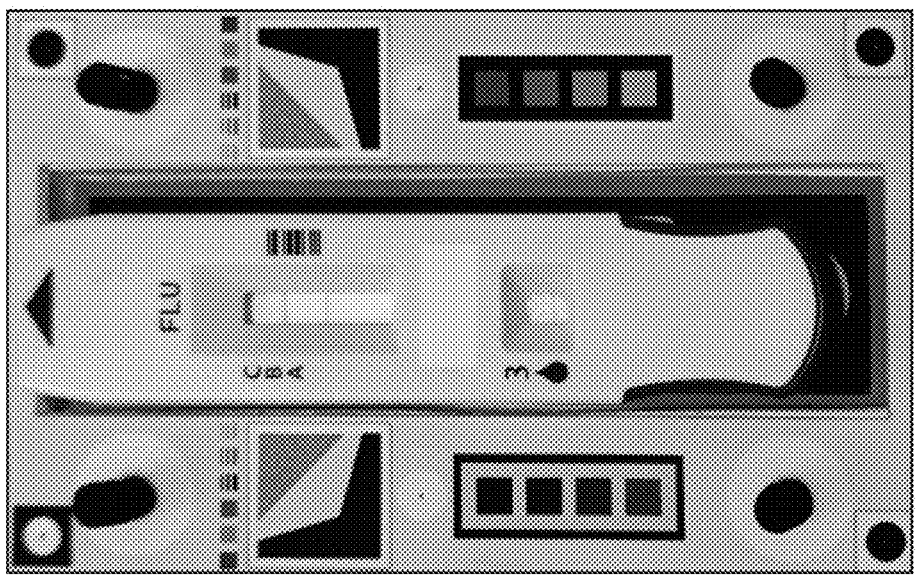
FIG. 8 is a de-warped version of the image of FIG. 7 generated by the image analysis software disclosed herein based on the fiducials of the 3D cartridge background device.

FIG. 8 is a de-warped version of the image of FIG. 7 generated by the image analysis software disclose herein based on the fiducials of the 3D cartridge background device.

Figure 9:
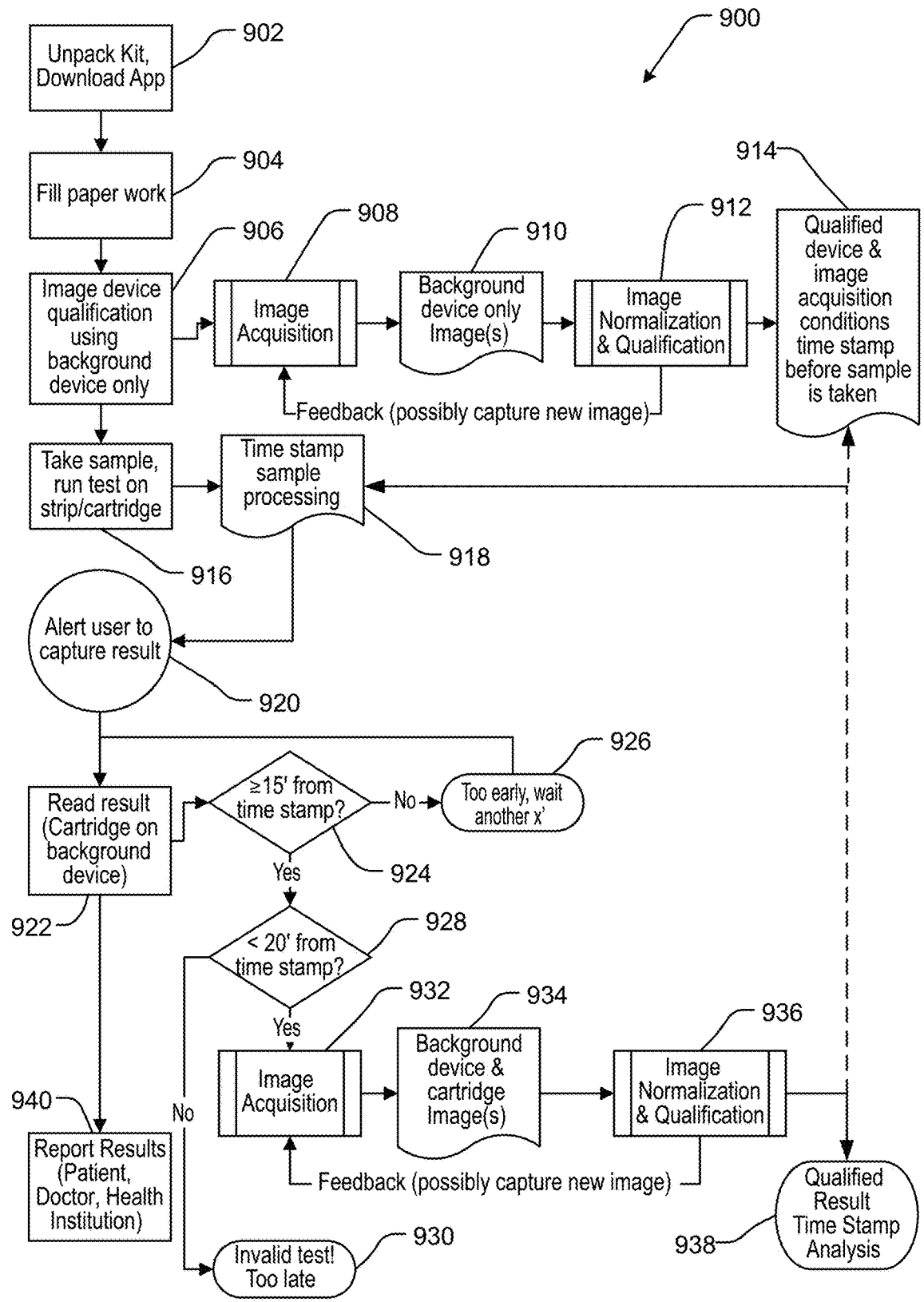
FIG. 9 is a flowchart illustrating an example method of performing and analyzing a test in accordance with the present technology.

FIG. 9 is a flowchart illustrating an example method 900 of performing and analyzing a test in accordance with the present technology. The method 900 may be performed at least in part by a clinician, health care provider, or other trained or untrained user performing a test in conjunction with one or more devices including an imaging device and a computing device comprising a processor and memory storing instructions that cause the processor to perform the computer-implemented operations described herein. In some embodiments, the one or more devices may include a smartphone, tablet, digital camera, or other computing device including the imaging device, processor, and memory. The method 900 is only one non-limiting example testing method, and the systems, devices, and methods of the present technology may equally be used in accordance with any other testing method. Advantageously, aspects of the method 900 can be performed by a user that does not have special training or expertise in performing tests. For example, the user can include an untrained operator that self-collects a sample and performs aspects of the method 900 in a non-clinical setting, such as the user's home. Accordingly, embodiments of the method 900 can include at-home collection by the individual being tested and display of results of the test to the individual in the at-home collection setting. It will be understood that the method 900 is not limited to at-home collection by the individual being tested, and that the tests of the present technology can be administered in any point-of-care (POC) setting (for example, doctor's offices, hospitals, urgent care centers and emergency rooms).

The method 900 begins at block 902, where a user opens a testing kit and downloads an application configured for the image normalization, qualification, and analysis described herein. In some embodiments, the testing kit may include a background device such as the 3D background device 100 disclosed herein, a cartridge such as the cartridge 200, and/or one or more test strips such as the test strip 205. The image acquisition and analysis application may be pre-installed on the user's computing device, or may be downloaded after opening the kit. For example, as described above with reference to FIG. 1A, in some embodiments the user may take an image of a QR code 145 or other computer-readable code located on the background device to cause the computing device to download the appropriate application. The QR code 145 or other computer-readable code on the background device may further cause the computing device to download additional supplemental data such as a background device model file and/or cartridge model file corresponding to the background device and/or the cartridge included in the kit. It will be understood that the location of the QR code 145 is not limited to the background device 100, and the QR code may be located in any suitable location, such as but not limited to test kit packaging and the cartridge 200.

At block 904, any necessary documentation associated with performance of the test may be completed by the user. At block 906, the user may perform one or more operations to qualify the imaging device, such as to determine if the imaging device and/or environmental conditions are suitable for capturing images for test analysis. At block 908, an image of the background device is captured without a cartridge present (that is, without a cartridge on the cartridge portion 104). At block 910, the application executing on the computing device obtains the image of the background device. At block 912, the application performs one or more image normalization and qualification operations, as will be described in greater detail below. Based on image normalization and qualification operations, the application may provide feedback or instructions to the user regarding the quality of the image, and may direct the user to capture a new image, for example, at a different angle or distance from the background device, under different lighting conditions, etc., based on the feedback or instructions from the application. If the image normalization and qualification operations determine that the imaging device is suitable, the method 900 continues to block 914 and the method 900 can continue to performing and analyzing the test.

At block 916, a sample, such as a biological sample, environmental sample, contaminant sample, or the like, is taken and applied to the cartridge (e.g., applied to a test strip 205 within cartridge 200 as shown in FIG. 2A either directly or indirectly, such as by placing the sample in a sample input well of the cartridge housing the test strip). At block 918, a time stamp is recorded associated with the beginning of the test processing time. In one example implementation, the user is prompted to take a picture of the background device prior to performing the test in order to ascertain whether the user, imaging device, and environmental conditions are adequate to perform the test and to unlock a time counter button to be selected when the test is being performed. The time counter button in various example embodiments may be a software button within a graphical user interface which, when pressed, may indicate that a test is being performed and may start a counter. The counter may be configured with one or more predetermined time thresholds corresponding to the test being performed. After a predetermined time, such as at or slightly before a predetermined initial test result threshold time, an alarm or other alert may be provided to the user at block 920 to inform the user that it is time to take a photograph of the test for result determination. For example, if the testing strip is configured to be read to provide an accurate result between 15 minutes and 20 minutes from application of the sample, the alert at block 920 may be provided at 14 minutes from the time stamp with an indication that the user should be ready to capture a result photograph in 1 minute.

At block 922, based on the alert provided at block 920, the user places the cartridge containing the test strip onto the background device and captures an image of a field of view containing the background device, the cartridge on the background device, and the test strip within the cartridge. Continuing to block 924, the application executing on the user's computing device determines whether the image was captured at a time greater than or equal to the initial test result threshold time (e.g., at least 15 minutes from the time stamp in this non-limiting example). If the image was not captured at least the initial threshold time after the time stamp, the method 900 continues to block 926, where the method 900 returns to block 922. The application may cause the computing device to provide an instruction to the user to wait an additional period of time (e.g., the time difference between the image capture time and the initial test result threshold time) before capturing another image of the background device and cartridge. If the image was captured at least the initial threshold time after the time stamp, the method continues to block 928.

At block 928, the application determines whether the image was captured prior to a test result expiration time (e.g., 20 minutes from the time stamp in this non-limiting example). If the image was not captured prior to the test result expiration time, the method 900 terminates at block 930, and may inform the user that the test is invalid because image acquisition occurred too late to accurately analyze the result. If the image was captured prior to the test result expiration time, the method 900 continues to block 932. In various embodiments, the application or other software may be configured to run multiple iterations of the method 900 at least partially simultaneously. The application or other software may include control, tracking, and/or individual test identification features to enable the tracking and verification to ensure that overlapping iterations of the method 900 are paired with the correct test strip 205 such as through registration of each test strip 205 and a start clock associated with the application of a sample to each test strip 205.

In blocks 932, 934, and 936, the application receives the image from the imaging device and performs image normalization and qualification processes, as will be described in greater detail with reference to FIGS. 10-11B, to determine if the image is suitable and, if the image is suitable, to determine a result of the test. At block 938, the application outputs a result. For example, if the image was captured within a required time window following test inoculation, image qualifying factors are acceptable, and the test is valid (e.g., the control line is visible), then the result may be considered valid. At block 940, the result of the test may be reported, such as by transmitting the result to a patient, doctor, health institution, or the like.

Figure 10:
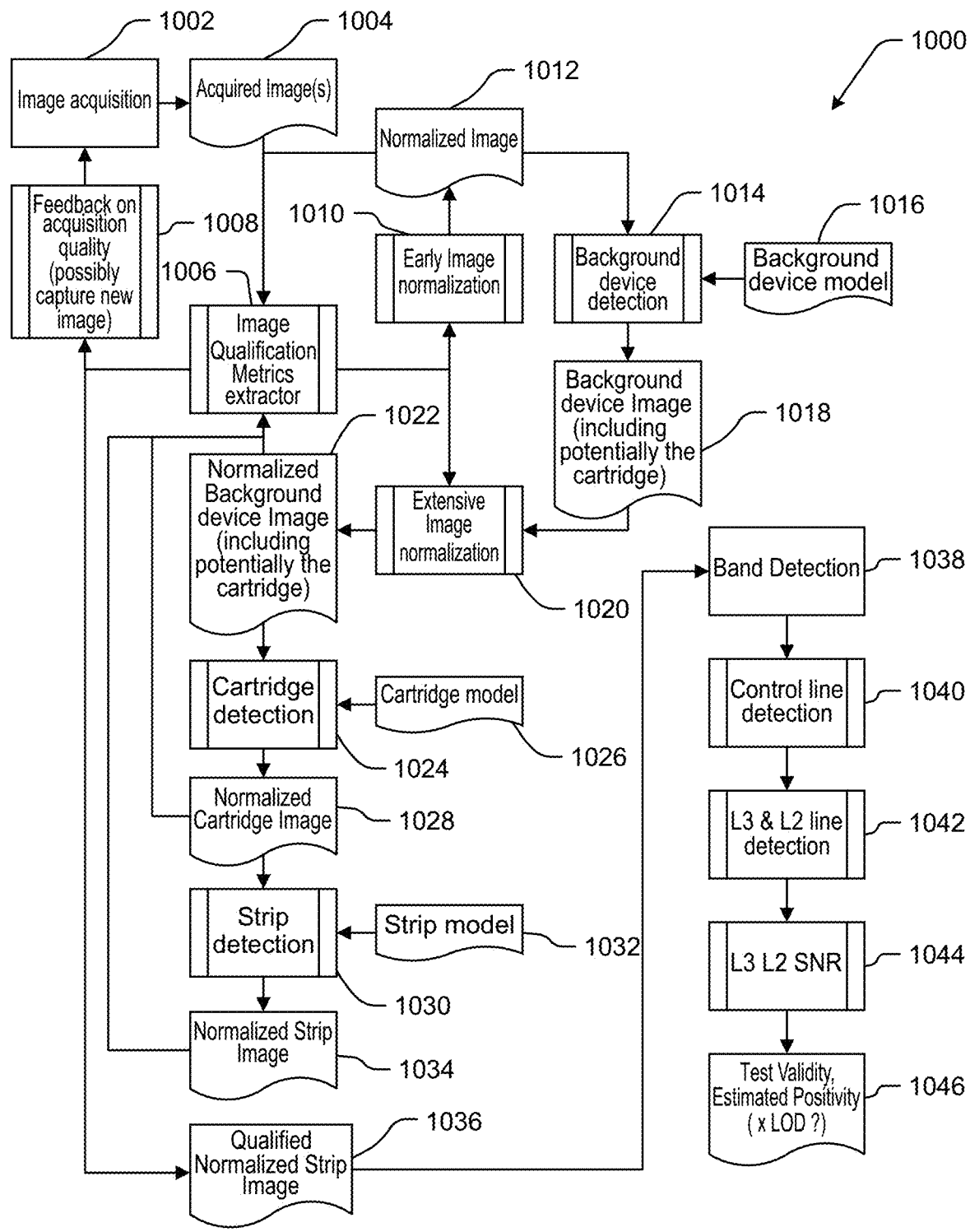
FIG. 10 is a flowchart illustrating an example method of acquiring and analyzing an image to determine a test result in accordance with the present technology.

FIG. 10 is a flowchart illustrating an example method 1000 of acquiring and analyzing an image to determine a test result in accordance with the present technology. Some or all of method 1000 may correspond to the operations performed, for example, to implement the image acquisition, normalization, and qualification operations of blocks 908-912 and/or blocks 932-936 of FIG. 9, as well as to the determination of results that may be reported at block 940. In some embodiments, the method 1000 may be performed at least in part by an application executing on a smartphone, tablet, digital camera, or other computing device including the imaging device, processor, and memory. The method 1000 is only one non-limiting example image acquisition and analysis method, and the systems, devices, and methods of the present technology may equally be used in accordance with any other testing method. Various example methods of image qualification and normalization may include less than all operations described in the method 1000, may include additional operations not described herein, and/or may include operations of method 1000 in the same or different order, without departing from the scope of the present disclosure. Moreover, while the method 1000 is described with reference to the 3D background device 100, cartridge 200, and test strip 205 illustrated in FIGS. 1A-2C, the operations of method 1000 may equally be implemented with any other background device, cartridge, and/or test strip.

The method 1000 begins at block 1002 with image acquisition. As described above with reference to the method 900, a user may obtain one or more images of a field of view including a background device such as 3D background device 100, a cartridge such as cartridge 200 on the background device, and/or a test strip such as test strip 205 within the cartridge. At block 1004, the application receives the one or more images from the imaging device. In some embodiments, the acquired images include an image of the background device without a cartridge thereon, and an image of the background device including the cartridge. At block 1006, an image qualification metrics extractor may identify features of an image to be used for image qualification and normalization. In some embodiments, the application may determine at block 1006 if the image is suitable for analysis (e.g., has sufficient illumination intensity, homogeneity, is in focus, and/or does not have excessive tilt and roll). If the image is not suitable, the method 1000 may continue to block 1008 to provide feedback to the user and possibly capture another, more suitable image based on the feedback. If the image is suitable for analysis, the method 1000 continues to block 1010.

At block 1010, the application performs early image normalization operations that can be performed based on the image alone without using a particular background device model. For example, the application may determine the boundaries of the background device (e.g., based on detecting one or more corners, edges, and/or viewing area fiducials of the background device). After identifying the portion of the image corresponding to the background device, the application may perform image normalization operations such as evaluating white balance and/or detecting glare from the surface of the background device that may inhibit accurate image analysis. At block 1012, the application can output an initial normalized image.

At block 1014, the application performs background device detection. In some embodiments, the application may detect a QR code, barcode, or other computer-readable indicia including identifying information specifying the type of background device and/or specifying a particular background device model that corresponds to the imaged background device. The application may then obtain the corresponding background device model 1016, such as from the memory of the computing device and/or from a remote computing device via a network connection. The method 1000 continues to block 1020, where more extensive image normalization operations may be performed based at least in part on an image of the background device (alone or with a cartridge received thereon) and on the obtained background device model corresponding to the background device. The image normalization operations performed at block 1020 may include operations based on various fiducials located on the background device (e.g., evaluation of illumination homogeneity, linearity, scaling, and other aspects), as will be described in greater detail with reference to FIGS. 11A and 11B. The image normalization operations performed at block 1020 are applied to at least the portion of the image containing the background device, to yield a normalized background device image 1022.

If the image includes a cartridge disposed on the background device, the method continues to block 1024, where the application performs cartridge detection. In some embodiments, the application may detect a QR code, barcode, or other computer-readable indicia including identifying information specifying the type of cartridge and/or specifying a particular cartridge model that corresponds to the imaged cartridge. The cartridge model 1026 corresponding to the imaged cartridge may be obtained, and the application may generate a normalized cartridge image 1028 based at least in part on the image and the cartridge model. In some embodiments, the normalized cartridge image 1028 may be generated based on the normalized background device image, by applying further image normalization operations to only the region of the image including the cartridge. The method 1000 may return to block 1006 to quality the normalized cartridge image 1028. The application may similarly detect the location and/or type of strip (e.g., test strip 205) disposed within the cartridge at block 1030, and may obtain a strip model 1032 corresponding to the detected strip, to generate a normalized strip image 1034 by applying further image normalization operations to only the region of the image including the strip.

The method 1000 may return to block 1006 to qualify the normalized strip image 1034, and the qualified normalized strip image 1036 may be analyzed at block 1038 by one or more band detection algorithms to detect the presence, intensity, color, and/or any other characteristics of visible bands on the test strip to determine a result of the test. In some embodiments, band detection may include detection of one or more control lines at block 1040, detection of one or more test lines at block 1042, a determination of signal to noise ratio (SNR) at the test lines at block 1044, and/or a determination of test validity and/or positivity at block 1046. The estimated positivity at block 1046 may be performed at least in part based on a known level of detection (LOD), which may be determined based on analysis of an image of the background device under the environmental conditions (e.g., lighting) present at the time of the test. For example, LOD may be determined based on a contrast assessment from a pixel resolution assessment of the background device area of the image, detection of test line fiducials 140 (FIG. 1A), a determined modulation transfer function from the background device, and/or noise evaluation based on linearity and/or noise determination (e.g., based on neutral patch fiducials 125).

Figure 11A:
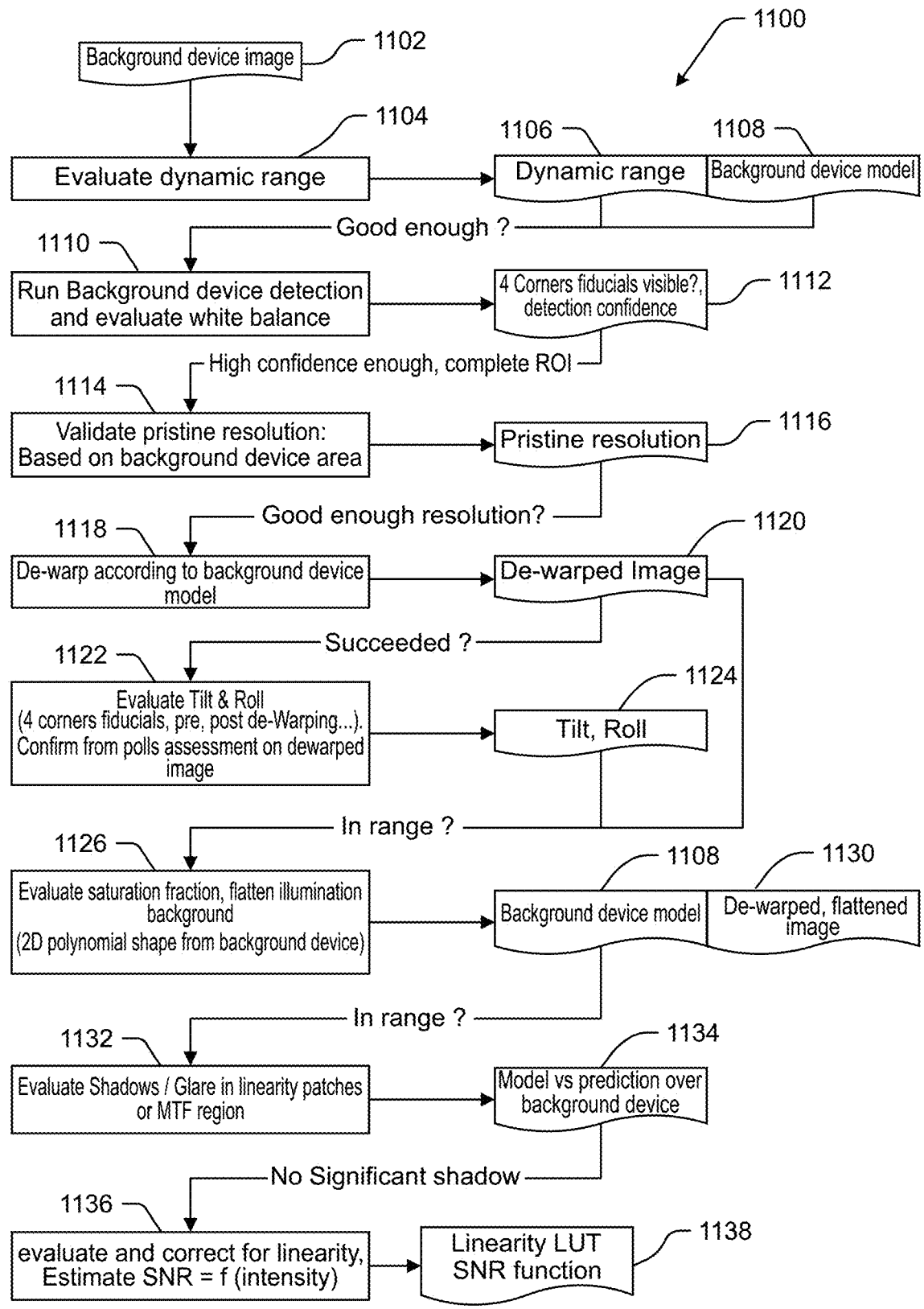
FIGS. 11A and 11B are a flowchart illustrating an example method of performing image qualification and normalization in accordance with the present technology.
Figure 11B:
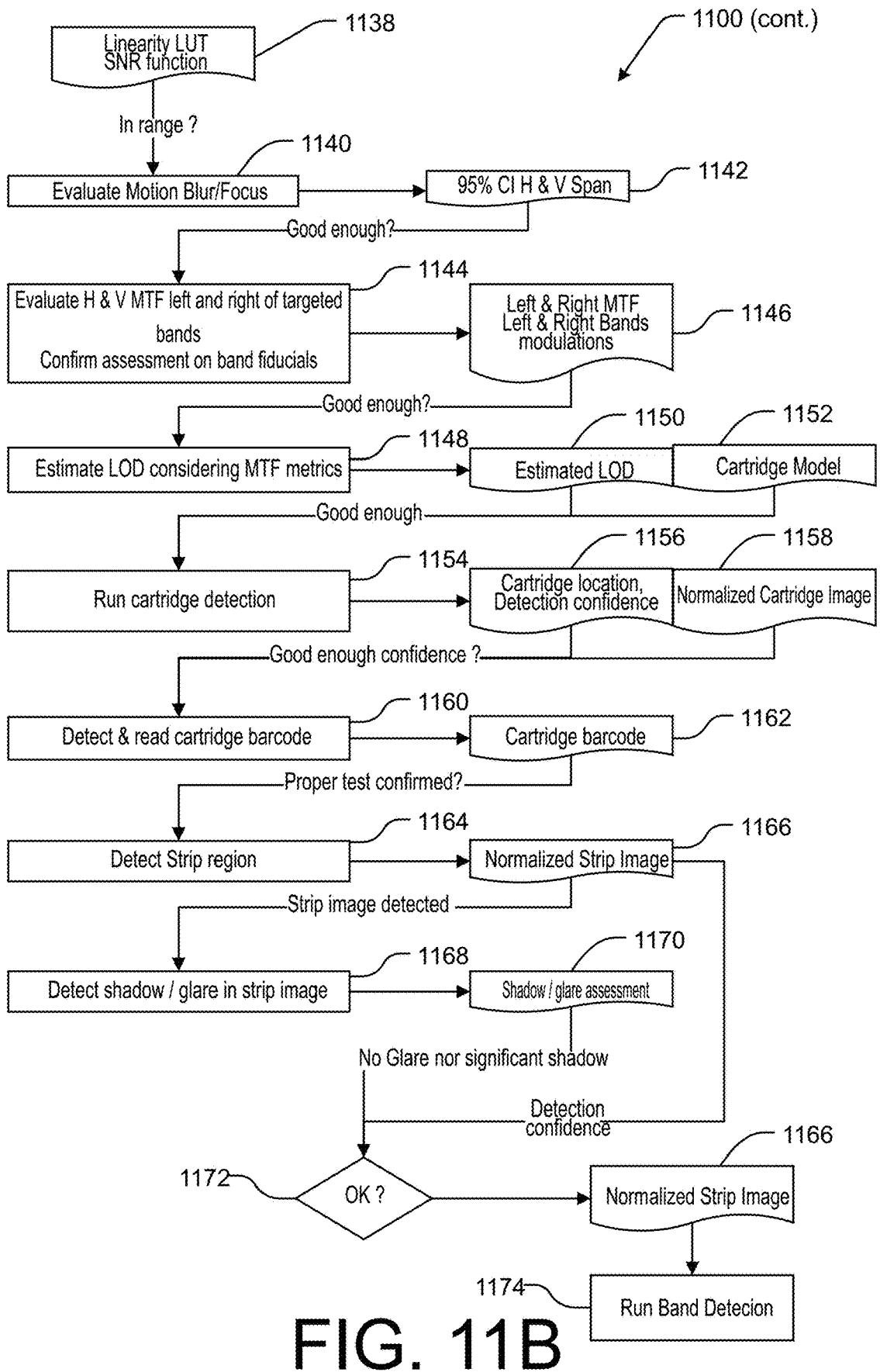

FIGS. 11A and 11B are a flowchart illustrating an example method 1100 of performing various image qualification and normalization operations in accordance with the present technology. Some or all of method 1100 may correspond to the operations performed, for example, to implement the image acquisition, normalization, and qualification operations of blocks 908-912 and/or blocks 932-936 of FIG. 9, as well as to the determination of results that may be reported at block 940. In some embodiments, the method 1100 may be performed at least in part by an application executing on a smartphone, tablet, digital camera, or other computing device including the imaging device, processor, and memory. The method 1100 is only one non-limiting example image qualification and normalization method, and the systems, devices, and methods of the present technology may equally be used in accordance with any other testing method. Various example methods of image qualification and normalization may include less than all operations described in the method 1100, may include additional operations not described herein, and/or may include operations of method 1100 in the same or different order, without departing from the scope of the present disclosure. Moreover, while the method 1100 is described with reference to the 3D background device 100, cartridge 200, and test strip 205 illustrated in FIGS. 1A-2C, the operations of method 1100 may equally be implemented with any other background device, cartridge, and/or test strip.

The method 1100 begins at block 1104 when an image 1102 is received for evaluation by the application. The field of view of the image 1102 includes a background device such as background device 100 (FIGS. 1A-2C). In some embodiments, the image 1102 may include the background device 100 with or without a cartridge 200 thereon. At block 1104, the application evaluates the dynamic range of the portion of the image corresponding to the background device 100, including or excluding the portion of the image corresponding to the cartridge 200. The application may evaluate the dynamic range in one, two, or all three of the red, green, and blue color channels. In some embodiments, it may be advantageous to evaluate the dynamic range in the green channel as a reference, as the green channel may contain the most information due to most Bayer patterns containing twice as many green pixels as blue or red pixels. Moreover, in embodiments in which the test strip 205 has reddish or red-hued control and test bands to be detected, it may be advantageous to calibrate the green and blue channels as those channels tend to have the greatest contrast at the locations of the bands. The application may output and/or store a dynamic range 1106 (e.g., as one or more values such as one or more numerical ranges and/or ratios) corresponding to some or all of the evaluated color channels, and/or may determine whether the determined dynamic range 1106 is within an acceptable range.

The method 1100 continues to block 1110, where the application performs background device detection and evaluates the white balance of the image. The application may identify a portion of the image 1102 containing the background device 100, such as by detecting one or more edges, corners, and/or fiducials of the background device 100. The application may determine a particular configuration of the background device 100 based on a background device model 1108 corresponding to the background device 100. In some embodiments, the appropriate background device model 1108 may be determined based on identifying a computer-readable identifier on the background device 100, and/or by selecting a corresponding background device model 1108 from among a plurality of available background device models corresponding to a variety of background device configurations.

The application may then perform a white balance evaluation on the portion of the image containing the background device 100. In some embodiments, the white balance evaluation may be performed based at least in part on the background device model 1108. For example, the background device model 1108 may indicate which portions of the background device are equally R,G,B balanced and therefore usable in the white balance evaluation. The application can thus evaluate the white balance of the background device portion of the image by identifying any difference among the red, green, and blue channels over the R,G,B balanced regions.

At block 1112, based on the background device model 1108, the application can determine whether the full region of interest (ROI) (e.g., the entire background device 100) is visible within the image 1102 (e.g., based on the detection of four corner fiducials 155 within the image 1102). The application may also determine a detection confidence level based at least in part on the evaluation of the white balance in the image 1102.

At block 1114, the application determines the pristine resolution of the image 1102, indicating a linear dimension of the area of the background device included within each pixel of the background device portion of the image. The background device model 1108 may include a known area of the imaged side of the background device 100 (e.g., length and width dimensions or a calculated area). The application may determine the number of pixels covering the background device portion of the image (e.g., based on the background device detection operations described above), and may thus determine a pristine resolution value 1116 by dividing a square root of the known background device area by the number of pixels representing the background device in the image. Thus, the determined pristine resolution value 1116 corresponds to the side length of the square area of the background device corresponding to each pixel in the image 1102. The application may further determine whether the determined pristine resolution value 1116 is within an acceptable range.

At block 1118, the application performs one or more de-warping operations to produce a de-warped image 1120 suitable for further analysis. For example, based at least in part on the background device model 1108, the application may determine one or more orientation characteristics such as tilt, roll, and/or distance of the background device relative to the imaging device that captured the image 1102. Some or all of these orientation characteristics may be determined as a linear or angular deviation from a standard or optimal orientation (e.g., an orientation in which the background device 100 is imaged along an axis perpendicular to the front surface of the background device at a predetermined distance with one or more edges of the background device 100 parallel to edges of the image). The application may further detect warping in the image due to, for example, imaging device lens effects, artifacts of other optics within the imaging device, motion during capture of the image, or the like. Based on the detected tilt, roll, distance, and/or other warping characteristics, the application edits the image 1102 to generate a de-warped image 1120 for further processing. At block 1122, the application may also compare the amount of tilt and roll in the original and/or de-warped images to determine if the tilt and roll are within an acceptable range. For example, a tilt and/or roll greater than a predetermined threshold value may result in different focus characteristics at different areas of the background device and/or cartridge, and may potentially cause portions of the 3D background device and/or cartridge to mask part of the image of the test strip.

At block 1126, the application evaluates the saturation of the background device portion of the image, and flattens the illumination of the background device in the image. For example, the application may apply a corrective factor comprising a second-degree polynomial fit to correct for illumination flatness in the image, to produce a de-warped, flattened image 1130. In some embodiments, any saturated pixel (e.g., a value of 255 corresponding to the maximum pixel intensity value in an 8-bit image) may be kept unchanged independently of the flattening for further glare assessment.

After correcting the illumination flatness of the image, at block 1132 the application evaluates the presence of shadow or glare on the background device. In one example, the application uses the background device model 1108 in conjunction with the de-warped, flattened image 1130 to identify the neutral patches 125 used for linearity assessment and/or the modulation transfer function regions 135 on the 3D background device 100. The appearance of these regions may be compared to an expected appearance based on the background device model 1108 to determine if excessive shadow and/or glare are present within the image. The application may generate a result 1134 indicating the effect of any shadow or glare on the de-warped, flattened image 1130.

At block 1136, the application evaluates the linearity of the intensity response in each color channel based on the neutral patches 125. In some embodiments, each of the neutral patches 125 comprise an equally white-balanced hue. The neutral patches 125 can be arranged to form a series or patches having linearly ascending intensity values such that the linearity of each channel can be evaluated. Based on the evaluation of linearity, the application can apply a correction for any detected nonlinearity, and can further estimate a signal to noise ratio (SNR) as a function of the normalized and linearized intensity. The application can then output and/or save a linearity lookup table (LUT) at block 1138 corresponding to the SNR at various intensity values.

Continuing to FIG. 11B, following the linearity assessment at block 1136, the method 1100 continues to block 1140 to evaluate the focus of the image and any motion blur effects. An out-of-focus image and/or the presence of motion-induced blurring may be detected, for example, based on the white disks 130 containing a small black dot, or other appropriate fiducial having a detectable feature of a relatively small size. In the example of the 3D background device 100, the application may determine the lateral extent of the black dot within the white disks 130 in the x and y directions. In determining the extent of the black dot in the image, the application may determine a region 1142 in which the pixel values are within 5% of the expected intensity value based on the background device model 1108. The x and y effects of motion blur or focus may be compared to a predetermined threshold to determine if the amount of motion blur is acceptable. In some embodiments, one of the x or y directions may have a lower threshold, for example, in the direction along which the test strip 205 is oriented, as motion blur in that direction would tend to cause difficulty in determining the widths of detected bands on the test strip 205.

At block 1144, the application evaluates the modulation transfer function (MTF) of the imaging device that generated the image 1102. The MTF may be assessed using regions 135 including slanted edges configured for horizontal and vertical MTF assessments. The MTF assessment may be repeated at two sides of the background device 100 on opposite sides of the location of the test strip 205. Regions 135 may be located substantially coplanar with the surface of the test strip 205 such that the application can estimate the mean MTF expected at the strip level where control and/or test bands are to be detected. MTF as a function of spatial frequency (MTF(f)) can be derived from the slanted edges of regions 135 using a process such as the ISO 12233 standard or other suitable mathematical processes. MTF metrics 1146 may be saved for use in estimating the level of detection (LOD) for image-based test analysis. The application may further confirm the assessment of the MTF based on the test band fiducials 140.

At block 1148, the application estimates the LOD based on the determined MTF metrics. Using a cartridge 200 with known antigen loads imaged in various imaging conditions (different phones and illumination intensities and environmental conditions), considering the median band width, it is possible to map out the expected original contrast of the test band once normalized according to the evaluated contrast MTF measured in the captured image. Considering a lower detection limit (e.g., 0.5%) and the known width and native contrast of known antigen loads it is therefore possible to estimate the expected LOD considering observed image quality (from measured metrics using background device fiducials). Thus, the LOD may be determined as a theoretical antigen load such that the test band contrast degraded according to MTF evaluation, is equal to the lower detection limit. The application may output or save the estimated LOD 1150.

The method 1100 continues to block 1154, where the application performs cartridge detection to detect a cartridge 200 located on the background device. The application may identify a portion of the de-warped, flattened image 1130 containing the cartridge 200, such as by selecting a portion of the image corresponding to a cartridge area indicated in the background device model 1108. The application may determine a particular configuration, test type, or other characteristic of the cartridge 200 based on a cartridge model 1152 corresponding to the cartridge 200. In some embodiments, the appropriate cartridge model 1152 may be determined based on identifying a computer-readable identifier on the cartridge 200, and/or by selecting a corresponding cartridge model 1152 from among a plurality of available cartridge models corresponding to a variety of cartridges compatible with the background device 100. The application may thus determine the cartridge location 1156 and/or a detection confidence of the cartridge location determination. The application may additionally perform one or more normalization operations on the cartridge portion of the image, based on the previous image normalization and analysis performed on the background device, to produce a normalized cartridge image 1158.

At block 1160, a barcode 1162 or other computer-readable identifier is detected and read from the cartridge to determine test information, such as a type of test, an antigen, contaminant, or condition detectable by the test, test and/or control band locations, and/or other information associated with determining a test result based on an image of the test strip 205. In some embodiments, the barcode may contain a test identifier, and the application may cause the test information to be retrieved from the memory of the computing device or from a remote memory, based on the test identifier.

At block 1164, the application can detect a region of the image corresponding to the test strip 205 to be analyzed. In some embodiments, the application can similarly perform one or more normalization operations on the strip portion of the image to produce a normalized strip image 1166 which can be analyzed to detect the presence of control and/or test bands. The application may further perform an additional shadow/glare detection operation at block 1168 to determine if any excessive shadow or glare is present on the test strip 205 that was not detected at the background device level. If the shadow/glare assessment result 1170 indicates that there is not a significant amount of glare or shadow that would affect the ability to determine a test result based on the image, the method continues to decision state 1172.

At decision state 1172, the application makes a final determination to proceed with test analysis. If the strip image 1166 is free of excessive glare and shadow, and the various normalization and qualification operations performed at the background device, cartridge, and test strip levels indicate that a test result can be obtained from the image of the test strip 205 with suitable confidence at an appropriate LOD, the method 1100 continues to block 1174, where one or more band detection algorithms are performed on the normalized strip image 1166 to identify the presence and location of a control band and/or any number of test bands on the test strip 205, as described above with reference to blocks 1038-1046 in the method 1000 of FIG. 10.

Figure 12B:
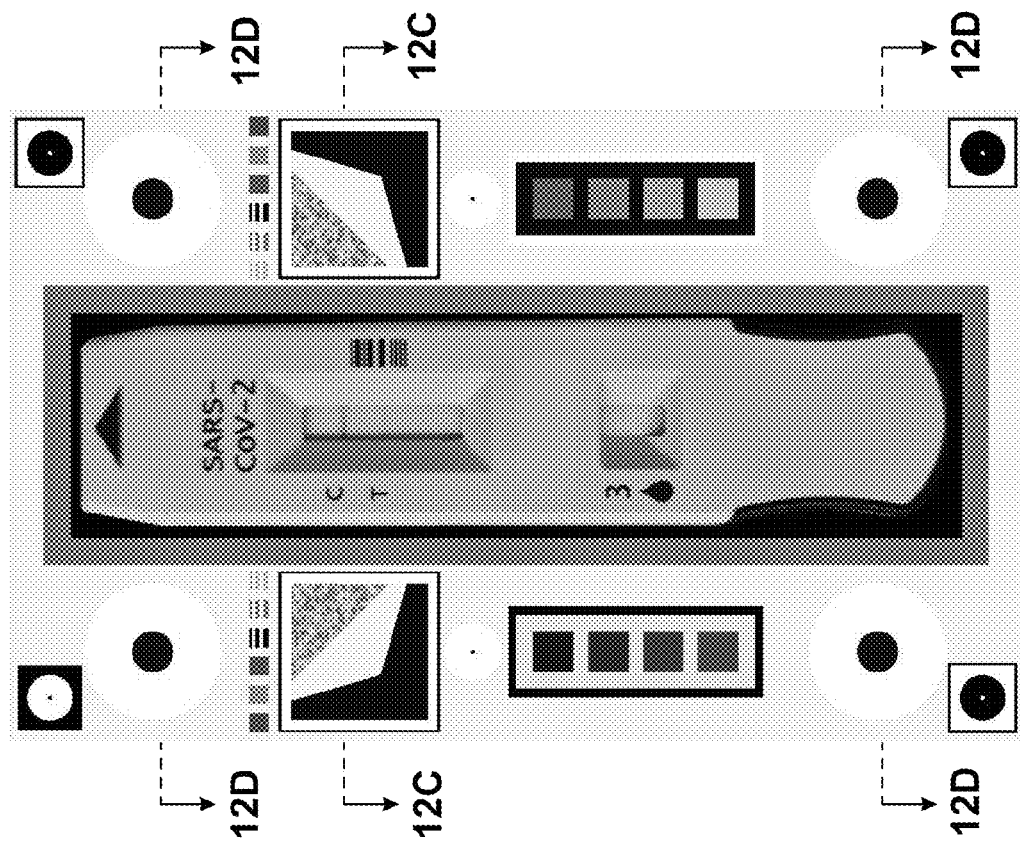
FIGS. 12A-12D illustrate an example cartridge background device in accordance with the present technology.
Figure 12A:
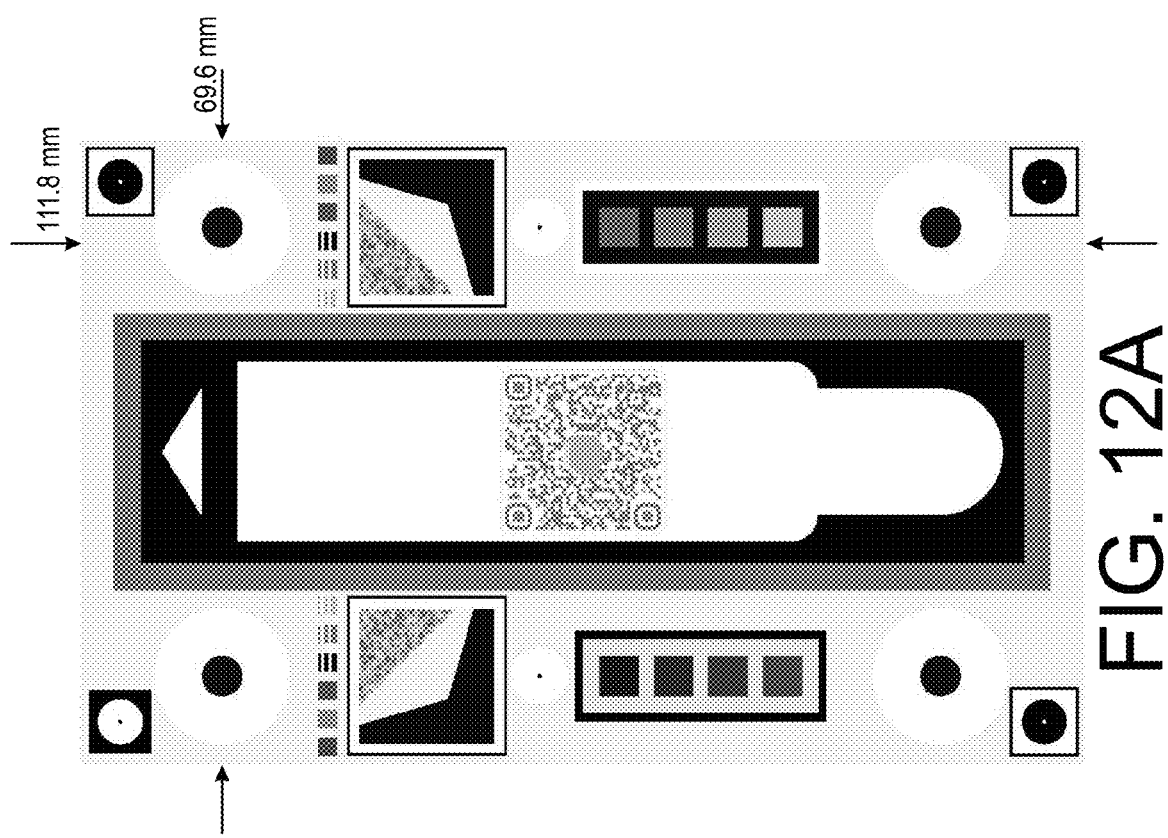
Figure 12C:
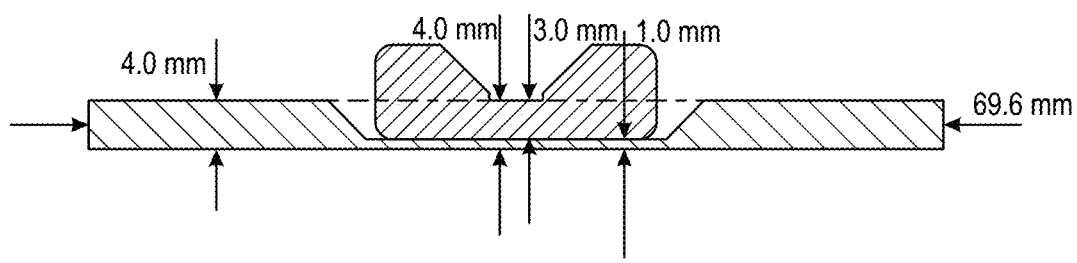
Figure 12D:
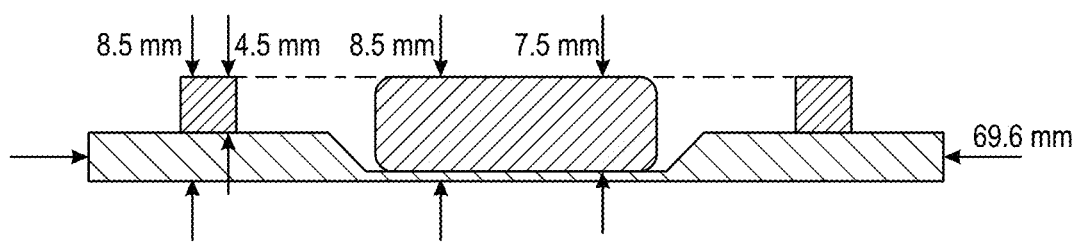

FIGS. 12A-12D illustrate a further example cartridge background device in accordance with the present technology, including exemplary non-limiting dimensions of the example device. FIG. 12A is an illustration of an example background device which is represented as a line drawing in FIG. 1A. FIG. 12B is an illustration of the example background device of FIG. 12A with an image of an actual test cartridge, both of which are represented in the line drawing of FIG. 2A.

Analytical devices described herein can accurately measure a plurality of analytes of interest in many different kinds of samples. Samples can include a specimen or culture obtained from any source, as well as biological and environmental samples. Biological samples may be obtained from animals (including humans) and encompass fluids, solids, tissues, and gases. Biological samples include urine, saliva, and blood products, such as plasma, serum and the like. Such examples are not however to be construed as limiting the sample types applicable to the present disclosure.

In some embodiments the sample is an environmental sample for detecting one or a plurality of analytes in the environment. In some embodiments, the sample is a biological sample from a subject. In some embodiments, a biological sample can include peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, or other lavage fluids.

As used herein, "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles, and metabolites of or antibodies to any of the above substances. Specific examples of some analytes include ferritin; creatinine kinase MB (CK-MB); human chorionic gonadotropin (hCG); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein (CRP); lipocalins; IgE antibodies; cytokines; TNF-related apoptosis-inducing ligand (TRAIL); vitamin B2 microglobulin; interferon gamma-induced protein 10 (IP-10); interferon-induced GTP-binding protein (also referred to as myxovirus (influenza virus) resistance 1, MX1, MxA, IFI-78K, IFI78, MX, MX dynamin like GTPase 1); procalcitonin (PCT); glycated hemoglobin (Gly Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Additional analytes may be included for purposes of biological or environmental substances of interest.

The present disclosure relates to lateral flow assay devices, test systems, and methods to determine the presence and concentration of a plurality of analytes in a sample, including when one or more analytes of interest are present at high concentrations and one or more analytes of interest are present at low concentrations. As discussed above, as used herein, "analyte" generally refers to a substance to be detected, for example a protein. Examples of proteins that can be detected by the lateral flow assay devices, test systems, and methods described herein include, without limitation:

TRAIL: TNF-related apoptosis-inducing ligand (also known as Apo2L, Apo-2 ligand and CD253); representative RefSeq DNA sequences are NC_000003.12; NC_018914.2; and NT_005612.17 and representative RefSeq Protein sequence accession numbers are NP_001177871.1; NP_001177872.1; and NP_003801.1. The TRAIL protein belongs to the tumor necrosis factor (TNF) ligand family.

CRP: C-reactive protein; representative RefSeq DNA sequences are NC_000001.11; NT_004487.20; and NC_018912.2 and a representative RefSeq Protein sequence accession numbers is NP_000558.2.

IP-10: Chemokine (C—X—C motif) ligand 10; representative RefSeq DNA sequences are NC_000004.12; NC_018915.2; and NT_016354.20 and a RefSeq Protein sequence is NP_001556.2.

PCT: Procalcitonin is a peptide precursor of the hormone calcitonin. A representative RefSeq amino acid sequence of this protein is NP_000558.2. Representative RefSeq DNA sequences include NC_000001.11, NT_004487.20, and NC_018912.2.

MX1: Interferon-induced GTP-binding protein Mx1 (also known as interferon-induced protein p78, Interferon-regulated resistance GTP-binding protein, MxA). Representative RefSeq amino acid sequences of this protein are NP_001138397.1; NM_001144925.2; NP_001171517.1; and NM_001178046.2.

Lateral flow assay devices, test systems, and methods according to the present disclosure can measure either the soluble and/or the membrane form of the TRAIL protein. In one embodiment, only the soluble form of TRAIL is measured.

The previous description of the disclosed implementations is provided to enable any person skilled in the art to make or use the present technology. Various modifications to these implementations will be readily apparent to those skilled in the art, and the generic principles defined herein may be applied to other implementations without departing from the spirit or scope of the present technology. Thus, the present technology is not intended to be limited to the implementations shown herein but is to be accorded the widest scope consistent with the principles and novel features disclosed herein.

What is claimed is:

1. A background device for an assay test strip, the background device comprising:
   a test strip portion sized and shaped to guide placement, on the background device, of a lateral flow assay test strip;
   a background portion at least partially surrounding the test strip portion;
   a plurality of line detection fiducials disposed on the background portion, each of the plurality of line detection fiducials having a color that is different than a color of a surrounding area of the background portion and a width associated with an expected width of a line on the lateral flow assay test strip; and
   one or more additional fiducials disposed on the background portion for evaluation of a modulation transfer function of an image capture device.

2. The background device of claim 1, wherein the plurality of line detection fiducials includes at least a first line detection fiducial having a width substantially equal to the expected width and a second line detection fiducial having a width greater than or less than the expected width.

3. The background device of claim 1, wherein the plurality of line detection fiducials includes at least a first line detection fiducial and a second line detection fiducial having a first shade of a color.

4. The background device of claim 3, wherein the plurality of line detection fiducials includes at least a third line detection fiducial having a second shade of the color that is lighter or darker than the first shade of the color.

5. The background device of claim 4, wherein the color is grey and an expected color of the line on the lateral flow assay test strip is not grey.

6. The background device of claim 1, further comprising one or more motion blur detection fiducials, each of the one or more motion blur detection fiducials comprising a dot of a first color surrounded by a region of a second color contrasting with the first color.

7. The background device of claim 1, further comprising at least three position fiducials disposed on the background portion proximate to corners of the background portion to facilitate detection of at least one of a position, tilt, or roll of an image capture device relative to the background device.

8. The background device of claim 1, wherein the background portion comprises a red-green-blue (RGB) balanced area having a color corresponding to equal red, green, and blue values in an RGB color space.

9. The background device of claim 1, wherein the test strip portion comprises alignment indicia configured to facilitate placement of the lateral flow assay test strip on the test strip portion of the background device.

10. The background device of claim 1, wherein the test strip portion comprises a computer-readable code positioned to be covered when the lateral flow assay test strip is placed on the test strip portion, the computer-readable code identifying a software application configured to analyze, based at least in part on the line detection fiducials, whether an image of the lateral flow assay test strip qualifies for further analysis.

11. The background device of claim 1, wherein the test strip portion comprises a computer-readable code positioned to be covered when the lateral flow assay test strip is placed on the test strip portion, the computer-readable code identifying a software application configured to analyze an image of the lateral flow assay test strip to determine a test result based at least in part on the line detection fiducials.

12. The background device of claim 1, wherein the background device is a 3-dimensional background device comprising one or more recesses or one or more 3-dimensional features protruding from the background portion.

13. The background device of claim 1, wherein the lateral flow assay test strip is housed in a cartridge, and wherein the test strip portion is sized and shaped to guide placement of the cartridge on the test strip portion of the background device.

14. The background device of claim 1, wherein each of the plurality of line detection fiducials has a width associated with an expected width of at least one of:

a test line that changes intensity or color in the presence of an analyte of interest in a sample applied to the lateral flow assay test strip; and a control line that changes intensity or color in the presence of the sample applied to the lateral flow assay test strip.

15. The background device of claim 1, wherein the one or more additional fiducials comprise at least one region having a color that is different than a color of a surrounding area of the background portion and at least one contrasting edge slanted relative to a dimension of the background device.

16. The background device of claim 15, wherein the at least one contrasting edge comprises a first contrasting edge disposed at a first slant angle for evaluation of an X-axis modulation transfer function and a second contrasting edge disposed at a second slant angle for evaluation of a Y-axis modulation transfer function.

17. A computer-implemented method of determining a test result, the method comprising:

capturing, by an image capture device, an image of a lateral flow assay test strip disposed on a test strip portion of a background device, the background device comprising a background portion at least partially surrounding the test strip portion;

detecting, by one or more processors based at least in part on the image, a plurality of line detection fiducials disposed on the background portion of the background device, each of the plurality of line detection fiducials having a color that is different than a color of a surrounding area of the background portion and a width associated with an expected width of a line on the lateral flow assay strip;

evaluating, by the one or more processors, a modulation transfer function of the image capture device based at least in part on one or more additional fiducials on the background portion of the background device;

detecting, by the one or more processors based at least in part on the image, one or more control lines or test lines on the lateral flow assay test strip based at least in part on the plurality of line detection fiducials; and determining, by the one or more processors, a test result of the lateral flow assay test strip based at least in part on the one or more detected control lines or test lines.

18. The computer-implemented method of claim 17, further comprising, prior to capturing the image, analyzing that an image taken by the image capture device qualifies or does not qualify for detection of the test result.

19. The computer-implemented method of claim 17, wherein detecting one or more control lines or test lines comprises detecting a presence of the one or more control lines or test lines based at least in part on a width of at least one of the plurality of line detection fiducials.

20. The computer-implemented method of claim 17, wherein the plurality of line detection fiducials includes at least a first line detection fiducial and a second line detection fiducial having a first shade of a color and a third line detection fiducial having a second shade of the color that is lighter or darker than the first shade of the color, and wherein detecting one or more control lines or test lines comprises detecting an intensity or a color of the one or more control lines or test lines based at least in part on the first, second, or the third line detection fiducial.

21. The computer-implemented method claim 20, wherein the color of the first, second, and third fiducial is grey and the color of the one or more control lines or test lines is not grey.

22. The computer-implemented method of claim 17, wherein the background portion of the background device comprises a red-green-blue (RGB) balanced area having a color corresponding to equal red, green, and blue values in an RGB color space.

23. The computer-implemented method of claim 22, further comprising, prior to determining the test result, evaluating an illumination condition of the background device based at least in part on the RGB balanced area.

24. The computer-implemented method of claim 23, wherein evaluating the illumination condition comprises detecting at least one of a glare or a shadow on the RGB balanced area.

25. The computer-implemented method of claim 17, further comprising estimating a level of detection based on the modulation transfer function, wherein the test result of the lateral flow assay is determined based at least in part on the estimated level of detection.

26. The computer-implemented method of claim 17, further comprising, prior to determining the test result, detecting a level of motion blur of the image based at least in part on one or more motion blur detection fiducials disposed on the background portion of the background device.

27. The computer-implemented method of claim 26, wherein each of the one or more motion blur detection fiducials comprises a dot of a first color surrounded by a region of a second color contrasting with the first color.

28. The computer-implemented method of claim 17, further comprising, prior to determining the test result, determining at least one of a position, a tilt, or a roll of the image capture device relative to the background device based at least in part on a plurality of position fiducials disposed on the background portion of the background device.

29. The computer-implemented method of claim 17, wherein the one or more additional fiducials comprise at least one region having a color that is different than a color of a surrounding area of the background portion and at least one contrasting edge slanted relative to a dimension of the background device.

30. The computer-implemented method of claim 29, wherein the at least one contrasting edge comprises a first contrasting edge disposed at a first slant angle for evaluation of an X-axis modulation transfer function and a second contrasting edge disposed at a second slant angle for evaluation of a Y-axis modulation transfer function.

* * * * *